United States Patent
Vind et al.

(10) Patent No.: US 10,465,172 B2
(45) Date of Patent: Nov. 5, 2019

(54) PEROXYGENASE VARIANTS

(71) Applicant: Novozymes A/S, Bagsvaerd (DK)

(72) Inventors: Jesper Vind, Vaerlose (DK); Lars Henrik Oestergaard, Charlottenlund (DK); Leonardo DeMaria, Frederiksberg (DK); Lisbeth Kalum, Vaerlose (DK); Eleni Amourgi, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/039,914

(22) PCT Filed: Dec. 1, 2014

(86) PCT No.: PCT/EP2014/076107
§ 371 (c)(1),
(2) Date: May 27, 2016

(87) PCT Pub. No.: WO2015/079064
PCT Pub. Date: Jun. 4, 2015

(65) Prior Publication Data
US 2016/0376566 A1    Dec. 29, 2016

(30) Foreign Application Priority Data
Nov. 29, 2013 (EP) .................................. 13195212

(51) Int. Cl.
| | |
|---|---|
| *C12N 9/08* | (2006.01) |
| *C12N 1/21* | (2006.01) |
| *C12N 15/53* | (2006.01) |
| *C12P 7/04* | (2006.01) |
| *C12P 7/26* | (2006.01) |
| *C12P 7/64* | (2006.01) |
| *C12P 7/02* | (2006.01) |
| *C12P 7/24* | (2006.01) |

(52) U.S. Cl.
CPC .............. *C12N 9/0065* (2013.01); *C12P 7/02* (2013.01); *C12P 7/24* (2013.01); *C12P 7/26* (2013.01); *C12P 7/6409* (2013.01); *C12Y 111/02001* (2013.01)

(58) Field of Classification Search
None
See application file for complete search history.

(56) References Cited

U.S. PATENT DOCUMENTS

| | | | | |
|---|---|---|---|---|
| 2010/0279366 A1* | 11/2010 | Pecyna | ................ | C12N 9/0065 435/122 |
| 2013/0017584 A1* | 1/2013 | Hofrichter | ................ | C12P 7/04 435/146 |

FOREIGN PATENT DOCUMENTS

| | | | |
|---|---|---|---|
| DE | 10332065 A1 | 1/2005 | |
| WO | 2006/034702 A1 | 4/2006 | |
| WO | 2007/020428 A1 | 2/2007 | |
| WO | 2008/119780 A2 | 10/2008 | |
| WO | 2011/120938 A2 | 10/2011 | |
| WO | WO-2014015256 A2 * | 1/2014 | ..... C12Y 101/03009 |
| WO | WO-2014090940 A1 * | 6/2014 | ......... C11D 3/38627 |

OTHER PUBLICATIONS

Bowie et al., Identifying determinants of folding and activity for a protein of unknown structure, Proc. Natl. Acad. Sci. USA, 1989, 86, 2152-56.*
European Patent Application No. 12197374.7 filed Dec. 14, 2012.*
Uniprot, Accession No. B9W4V6, 2013, www.uniprot.org.*
Anh et al., Applied and Environmental Microbiology, vol. 73, No. 17, pp. 5477-5485 (2007).
Cirino et al., Adv. Synth. Catal., vol. 344, No. 9, pp. 932-937 (2002).
Cirino et al., Biotechnology and Bioengineering, vol. 83, No. 6, pp. 729-734 (2003).
Hofricther et al., EBI Accession No. AZN34538 (2011).
Kluge et al., Appl. Microbiol. Biotechnol., vol. 75, pp. 1473-1478 (2007).
Salazar et al., ChemBioChem, vol. 4, No. 9, pp. 891-893 (2003).
Savenkova et al., Archives of Biochemistry and Biophysics, vol. 351, No. 2, pp. 286-293 (1998).
Savenkova et al., Biochemistry, vol. 37, No. 30, pp. 10828-10836 (1998).
Ullrich et al., FEBS Lett, vol. 579, pp. 6247-6250 (2005).

* cited by examiner

*Primary Examiner* — Robert B Mondesi
*Assistant Examiner* — Todd M Epstein
(74) *Attorney, Agent, or Firm* — Eric J. Fechter

(57) ABSTRACT

The present invention relates to peroxygenase variants. The present invention also relates to polynucleotides encoding the variants; nucleic acid constructs, vectors, and host cells comprising the polynucleotides; and methods of using the variants.

21 Claims, No Drawings
Specification includes a Sequence Listing.

SEQUENCE LISTING

```
<160> NUMBER OF SEQ ID NOS: 2

<210> SEQ ID NO 1
<211> LENGTH: 1089
<212> TYPE: DNA
<213> ORGANISM: Coprinopsis cinerea
<220> FEATURE:
<221> NAME/KEY: CDS
<222> LOCATION: (1)..(1086)

<400> SEQUENCE: 1 ttc cct gca tac gcc tcc ttg gga ggc ttg acc gaa cgt cag gtg gag       48
Phe Pro Ala Tyr Ala Ser Leu Gly Gly Leu Thr Glu Arg Gln Val Glu
1               5                   10                  15 gag tat acg tcg aag ttg cct atc gtg ttc cct cct cct ccg gaa           96
Glu Tyr Thr Ser Lys Leu Pro Ile Val Phe Pro Pro Pro Pro Glu
            20                  25                  30 cct atc aaa gat cct tgg ctc aag ctc gtg aac gat agg gca cac ccc      144
Pro Ile Lys Asp Pro Trp Leu Lys Leu Val Asn Asp Arg Ala His Pro
        35                  40                  45 tgg agg cct ttg agg cga ggc gac gtg cga gga ccc tgt ccc ggt ctc      192
Trp Arg Pro Leu Arg Arg Gly Asp Val Arg Gly Pro Cys Pro Gly Leu
    50                  55                  60
```

|  |  |
|---|---|
| aac acc ctc gca tcc cat ggc tat ttg cct cgc gac ggc gtc gcc aca<br>Asn Thr Leu Ala Ser His Gly Tyr Leu Pro Arg Asp Gly Val Ala Thr<br>65                          70                    75                   80 | 240 |
| ccg gca cag atc atc aca gcg gtc cag gaa ggc ttc aac atg gaa tac<br>Pro Ala Gln Ile Ile Thr Ala Val Gln Glu Gly Phe Asn Met Glu Tyr<br>                       85                    90                   95 | 288 |
| ggc atc gcc aca ttc gtc acc tat gca gcc cac ctc gtg gac gga aac<br>Gly Ile Ala Thr Phe Val Thr Tyr Ala Ala His Leu Val Asp Gly Asn<br>                100                  105                110 | 336 |
| ccg ctc acc aac ttg atc tcc att gga ggc aag acc cgg aaa act ggt<br>Pro Leu Thr Asn Leu Ile Ser Ile Gly Gly Lys Thr Arg Lys Thr Gly<br>              115                  120                125 | 384 |
| ccg gac cct cct cct cct gcg atc gtg gga gga ttg aac aca cat gcg<br>Pro Asp Pro Pro Pro Pro Ala Ile Val Gly Gly Leu Asn Thr His Ala<br>130                        135                  140 | 432 |
| gtc ttc gag ggc gac gcg tcc atg aca cga ggc gat ttc cat ttg ggt<br>Val Phe Glu Gly Asp Ala Ser Met Thr Arg Gly Asp Phe His Leu Gly<br>145                        150                  155                160 | 480 |
| gac aac ttc aac ttc aac cag act ctc tgg gag cag ttc aag gat tac<br>Asp Asn Phe Asn Phe Asn Gln Thr Leu Trp Glu Gln Phe Lys Asp Tyr<br>                165                  170                175 | 528 |
| tcg aac cgc tat ggt gga gga agg tat aac ctc act gca gca gcc gag<br>Ser Asn Arg Tyr Gly Gly Gly Arg Tyr Asn Leu Thr Ala Ala Ala Glu<br>              180                  185                190 | 576 |
| ttg cgt tgg gca cga atc cag cag tcc atg gca acc aac gga cag ttc<br>Leu Arg Trp Ala Arg Ile Gln Gln Ser Met Ala Thr Asn Gly Gln Phe<br>            195                  200                205 | 624 |
| gac ttc acc tcg ccc agg tac ttc aca gcc tat gcc gaa tcc gtg ttc<br>Asp Phe Thr Ser Pro Arg Tyr Phe Thr Ala Tyr Ala Glu Ser Val Phe<br>210                        215                  220 | 672 |
| cct atc aac ttc ttc acc gac gga cga ttg ttc acc tcg aac acc act<br>Pro Ile Asn Phe Phe Thr Asp Gly Arg Leu Phe Thr Ser Asn Thr Thr<br>225                        230                  235                240 | 720 |
| gca cct gga ccc gac atg gat tcg gcg ttg tcg ttc ttc cga gac cac<br>Ala Pro Gly Pro Asp Met Asp Ser Ala Leu Ser Phe Phe Arg Asp His<br>                    245                  250                255 | 768 |
| agg tat ccg aaa gat ttc cat cga gcg cct gtc cct tcg ggt gca cgg<br>Arg Tyr Pro Lys Asp Phe His Arg Ala Pro Val Pro Ser Gly Ala Arg<br>            260                  265                270 | 816 |
| gga ttg gac gtc gtc gca gca gcg tac ccc att cag cct ggc tac aac<br>Gly Leu Asp Val Val Ala Ala Ala Tyr Pro Ile Gln Pro Gly Tyr Asn<br>            275                  280                285 | 864 |
| gcc gat ggc aag gtc aac aac tat gtc ttg gac ccc acg tcc gca gat<br>Ala Asp Gly Lys Val Asn Asn Tyr Val Leu Asp Pro Thr Ser Ala Asp<br>290                        295                  300 | 912 |
| ttc acc aag ttc tgt ctc ttg tac gag aac ttc gtg ttg aag acc gtc<br>Phe Thr Lys Phe Cys Leu Leu Tyr Glu Asn Phe Val Leu Lys Thr Val<br>305                        310                  315                320 | 960 |
| aag ggt ttg tac ccc aac cct aag ggc ttc ctc agg aag gcg ttg gag<br>Lys Gly Leu Tyr Pro Asn Pro Lys Gly Phe Leu Arg Lys Ala Leu Glu<br>            325                  330                335 | 1008 |
| aca aac ttg gag tat ttc tac cag tcc ttc cct ggc tcc ggt ggc tgt<br>Thr Asn Leu Glu Tyr Phe Tyr Gln Ser Phe Pro Gly Ser Gly Gly Cys<br>            340                  345                350 | 1056 |
| ccc cag gtg ttc ccc tgg ggt aag tcg gat tag<br>Pro Gln Val Phe Pro Trp Gly Lys Ser Asp<br>            355                  360 | 1089 |

<210> SEQ ID NO 2
<211> LENGTH: 362

```
<212> TYPE: PRT
<213> ORGANISM: Coprinopsis cinerea

<400> SEQUENCE: 2

Phe Pro Ala Tyr Ala Ser Leu Gly Gly Leu Thr Glu Arg Gln Val Glu
  1               5                  10                  15

Glu Tyr Thr Ser Lys Leu Pro Ile Val Phe Pro Pro Pro Pro Glu
                 20                  25                  30

Pro Ile Lys Asp Pro Trp Leu Lys Leu Val Asn Asp Arg Ala His Pro
             35                  40                  45

Trp Arg Pro Leu Arg Arg Gly Asp Val Arg Gly Pro Cys Pro Gly Leu
         50                  55                  60

Asn Thr Leu Ala Ser His Gly Tyr Leu Pro Arg Asp Gly Val Ala Thr
 65                  70                  75                  80

Pro Ala Gln Ile Ile Thr Ala Val Gln Glu Gly Phe Asn Met Glu Tyr
                 85                  90                  95

Gly Ile Ala Thr Phe Val Thr Tyr Ala Ala His Leu Val Asp Gly Asn
                100                 105                 110

Pro Leu Thr Asn Leu Ile Ser Ile Gly Gly Lys Thr Arg Lys Thr Gly
            115                 120                 125

Pro Asp Pro Pro Pro Ala Ile Val Gly Gly Leu Asn Thr His Ala
        130                 135                 140

Val Phe Glu Gly Asp Ala Ser Met Thr Arg Gly Asp Phe His Leu Gly
145                 150                 155                 160

Asp Asn Phe Asn Phe Asn Gln Thr Leu Trp Glu Gln Phe Lys Asp Tyr
                165                 170                 175

Ser Asn Arg Tyr Gly Gly Arg Tyr Asn Leu Thr Ala Ala Ala Glu
            180                 185                 190

Leu Arg Trp Ala Arg Ile Gln Gln Ser Met Ala Thr Asn Gly Gln Phe
        195                 200                 205

Asp Phe Thr Ser Pro Arg Tyr Phe Thr Ala Tyr Ala Glu Ser Val Phe
210                 215                 220

Pro Ile Asn Phe Phe Thr Asp Gly Arg Leu Thr Ser Asn Thr Thr
225                 230                 235                 240

Ala Pro Gly Pro Asp Met Asp Ser Ala Leu Ser Phe Phe Arg Asp His
                245                 250                 255

Arg Tyr Pro Lys Asp Phe His Arg Ala Pro Val Pro Ser Gly Ala Arg
            260                 265                 270

Gly Leu Asp Val Val Ala Ala Tyr Pro Ile Gln Pro Gly Tyr Asn
        275                 280                 285

Ala Asp Gly Lys Val Asn Asn Tyr Val Leu Asp Pro Thr Ser Ala Asp
290                 295                 300

Phe Thr Lys Phe Cys Leu Leu Tyr Glu Asn Phe Val Leu Lys Thr Val
305                 310                 315                 320

Lys Gly Leu Tyr Pro Asn Pro Lys Gly Phe Leu Arg Lys Ala Leu Glu
            325                 330                 335

Thr Asn Leu Glu Tyr Phe Tyr Gln Ser Phe Pro Gly Ser Gly Gly Cys
        340                 345                 350

Pro Gln Val Phe Pro Trp Gly Lys Ser Asp
355                 360
```

PEROXYGENASE VARIANTS

CROSS-REFERENCE TO RELATED APPLICATIONS

This application is a 35 U.S.C. 371 national application of international application no. PCT/EP2014/076107 filed Dec. 1, 2014, which claims priority or the benefit under 35 U.S.C. 119 of European application no. 13195212.9 filed Nov. 29, 2013. The content of these applications is fully incorporated herein by reference.

REFERENCE TO A SEQUENCE LISTING

This application contains a Sequence Listing in computer readable form, which is incorporated herein by reference.

BACKGROUND

Field of the Invention

The present invention relates to peroxygenase variants, polynucleotides encoding the variants, methods of producing the variants, and methods of using the variants.

Description of the Related Art

WO 2006/034702 A1 discloses methods for the enzymatic hydroxylation of non-activated hydrocarbons, such as, naphtalene, toluol and cyclohexane, using the AaP peroxygenase enzyme of *Agrocybe aegerita* TM A1. This is also described in Ullrich and Hofrichter, 2005, FEBS Letters 579: 6247-6250.

DE 103 32 065 A1 discloses methods for the enzymatic preparation of acids from alcohols through the intermediary formation of aldehydes by using the AaP peroxygenase enzyme of *Agrocybe aegerita* TM A1.

A method was reported for the rapid and selective spectrophotometric direct detection of aromatic hydroxylation by the AaP peroxygenase (Kluge et al., 2007, Appl Microbiol Biotechnol 75: 1473-1478).

Another peroxygenase capable of aromatic peroxygenation was isolated from the coprophilous fungus *Coprinus radians* and characterized, the N-terminal 16 amino acids were identified and aligned with the N-terminal 14 amino acids of the AaP enzyme of the *A. aegerita* strain earlier published; but the encoding gene was not isolated (Anh et al., 2007, Appl Env Microbiol 73(17): 5477-5485).

WO 2008/119780 discloses several different peroxygenase polypeptides and their encoding polynucleotides, as well as recombinant production thereof.

WO 2011/120938 discloses site-specific hydroxylation of aliphatic hydrocarbons using peroxygenase polypeptides.

The present invention provides peroxygenase variants with improved properties compared to its parent.

SUMMARY OF THE INVENTION

The present invention relates to peroxygenase variants, comprising a substitution at one or more (e.g., several) positions corresponding to positions E16, Y18, P28, P31, W38, R50, Y72, F92, M94, I98, T100, H102, C103, Y104, H107, L114, A144, F146, M152, F163, Q167, Y180, T188, W195, M202, Y215, F216, S222, F224, F228, F229, M246, F253, H256, Y258, Y281, Y287, F308, L317, T319, S345, F346, P347, G348, S349, and G350; preferably M94, A144, Y180, W195, Y215, F224, F228, and F229 of the mature polypeptide of SEQ ID NO: 2, wherein the variants have peroxygenase activity.

The present invention also relates to polynucleotides encoding the peroxygenase variants; nucleic acid constructs, vectors, and host cells comprising the polynucleotides; and methods of producing the variants.

The present invention also relates to methods of using the peroxygenase variants.

Definitions

Peroxygenase: The term "peroxygenase" means an enzyme exhibiting "unspecific peroxygenase" activity according to EC 1.11.2.1, that catalyzes insertion of an oxygen atom from $H_2O_2$ into a variety of substrates, such as nitrobenzodioxole. For purposes of the present invention, peroxygenase activity is determined according to the procedure described in M. Poraj-Kobielska, M. Kinne, R. Ullrich, K. Scheibner, M. Hofrichter, "A spectrophotometric assay for the detection of fungal peroxygenases", *Analytical Biochemistry* (2012), vol. 421, issue 1, pp. 327-329.

The peroxygenase of the present invention has at least 20%, preferably at least 40%, more preferably at least 50%, more preferably at least 60%, more preferably at least 70%, more preferably at least 80%, even more preferably at least 90%, most preferably at least 95%, and even most preferably at least 100% of the peroxygenase activity of the mature polypeptide of SEQ ID NO: 2.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has peroxygenase activity.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, improved oxidation stability, improved storage stability, reduced catalase activity, reduced peroxidase activity, improved activity on veratryl alcohol, and improved activity on cyclohexane.

Catalase activity is an enzymatic activity according to EC 1.11.1.6.

Peroxidase activity is an enzymatic activity according to EC 1.11.1.7.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc.

Mature polypeptide coding sequence: The term "mature polypeptide coding sequence" means a polynucleotide that encodes a mature polypeptide having peroxygenase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent peroxygenase: The term "parent" or "parent peroxygenase" means a peroxygenase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having peroxygenase activity.

Variant: The term "variant" means a polypeptide having peroxygenase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the peroxygenase activity of the mature polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type peroxygenase: The term "wild-type" peroxygenase means a peroxygenase expressed by a naturally occurring microorganism, such as a bacterium, yeast, or filamentous fungus found in nature.

Conventions for Designation of Variants

For purposes of the present invention, the mature polypeptide disclosed in SEQ ID NO: 2 is used to determine the corresponding amino acid residue in another peroxygenase. The amino acid sequence of another peroxygenase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another peroxygenase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:39-64; Katoh and Toh, 2010, *Bioinformatics* 26: 1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions. For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. When the symbol "*" is used as the substituted amino acid, it means that the original amino acid has been substituted with nothing, i.e., the original amino acid has been deleted (a deletion).

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple alterations. Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

DETAILED DESCRIPTION

Peroxygenase Variants

The present invention relates to peroxygenase variants, comprising a substitution at one or more (e.g., several) positions corresponding to positions E16, Y18, P28, P31, W38, R50, Y72, F92, M94, I98, T100, H102, C103, Y104, H107, L114, A144, F146, M152, F163, Q167, Y180, T188, W195, M202, Y215, F216, S222, F224, F228, F229, M246, F253, H256, Y258, Y281, Y287, F308, L317, T319, S345, F346, P347, G348, S349, and G350; preferably M94, A144, Y180, W195, Y215, F224, F228, and F229 of the mature polypeptide of SEQ ID NO: 2, wherein the variant has peroxygenase activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent peroxygenase.

In another embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

In one aspect, the number of substitutions in the variants of the present invention is 1-20, e.g., 1-10 and 1-5, such as 1, 2, 3, 4, 5, 6, 7, 8, 9 or 10 substitutions.

In another aspect, a variant comprises a substitution at one or more (e.g., several) positions corresponding to positions M94, A144, Y180, W195, Y215, F224, F228, and F229. In another aspect, a variant comprises a substitution at two positions corresponding to any of positions M94, A144, Y180, W195, Y215, F224, F228, and F229. In another aspect, a variant comprises a substitution at three positions corresponding to any of positions M94, A144, Y180, W195, Y215, F224, F228, and F229. In another aspect, a variant comprises a substitution at four positions corresponding to any of positions M94, A144, Y180, W195, Y215, F224, F228, and F229. In another aspect, a variant comprises a substitution at five positions corresponding to any of positions M94, A144, Y180, W195, Y215, F224, F228, and F229. In another aspect, a variant comprises a substitution at six positions corresponding to any of positions M94, A144, Y180, W195, Y215, F224, F228, and F229. In another aspect, a variant comprises a substitution at seven positions corresponding to any of positions M94, A144, Y180, W195, Y215, F224, F228, and F229. In another aspect, a variant comprises a substitution at each position corresponding to positions M94, A144, Y180, W195, Y215, F224, F228, and F229.

In another aspect, the variant comprises or consists of a substitution at a position corresponding to position M94. In another aspect, the amino acid at a position corresponding to position M94 is substituted with Ala, Arg, Asn, Asp, Cys, Gln, Glu, Gly, His, Ile, Leu, Lys, Phe, Pro, Ser, Thr, Trp, Tyr, or Val, preferably with Phe. In another aspect, the variant comprises or consists of the substitution M94F of the mature polypeptide of SEQ ID NO: 2.

In another aspect, the variant comprises or consists of a substitution at a position corresponding to position A144. In another aspect, the amino acid at a position corresponding to position A144 is substituted with Arg, Asn, Asp, Cys, Gln, Glu, Gly, His, Ile, Leu, Lys, Met, Phe, Pro, Ser, Thr, Trp, Tyr, or Val, preferably with Arg. In another aspect, the variant comprises or consists of the substitution A144R of the mature polypeptide of SEQ ID NO: 2.

In another aspect, the variant comprises or consists of a substitution at a position corresponding to position Y180. In another aspect, the amino acid at a position corresponding to position Y180 is substituted with Ala, Arg, Asn, Asp, Cys, Gln, Glu, Gly, His, Ile, Leu, Lys, Met, Phe, Pro, Ser, Thr, Trp, or Val, preferably with Phe. In another aspect, the variant comprises or consists of the substitution Y180F of the mature polypeptide of SEQ ID NO: 2.

In another aspect, the variant comprises or consists of a substitution at a position corresponding to position W195. In another aspect, the amino acid at a position corresponding to position W195 is substituted with Ala, Arg, Asn, Asp, Cys, Gln, Glu, Gly, His, Ile, Leu, Lys, Met, Phe, Pro, Ser, Thr, Tyr, or Val, preferably with Phe. In another aspect, the variant comprises or consists of the substitution W195F of the mature polypeptide of SEQ ID NO: 2.

In another aspect, the variant comprises or consists of a substitution at a position corresponding to position Y215. In another aspect, the amino acid at a position corresponding to position Y215 is substituted with Ala, Arg, Asn, Asp, Cys, Gln, Glu, Gly, His, Ile, Leu, Lys, Met, Phe, Pro, Ser, Thr, Trp, or Val, preferably with Phe. In another aspect, the variant comprises or consists of the substitution Y215F of the mature polypeptide of SEQ ID NO: 2.

In another aspect, the variant comprises or consists of a substitution at a position corresponding to position F224. In another aspect, the amino acid at a position corresponding to position F224 is substituted with Ala, Arg, Asn, Asp, Cys, Gln, Glu, Gly, His, Ile, Leu, Lys, Met, Pro, Ser, Thr, Trp, Tyr, or Val, preferably with Leu or Gly. In another aspect, the variant comprises or consists of the substitution F224L,G of the mature polypeptide of SEQ ID NO: 2.

In another aspect, the variant comprises or consists of a substitution at a position corresponding to position F228. In another aspect, the amino acid at a position corresponding to position F228 is substituted with Ala, Arg, Asn, Asp, Cys, Gln, Glu, Gly, His, Ile, Leu, Lys, Met, Pro, Ser, Thr, Trp, Tyr, or Val, preferably with Leu. In another aspect, the variant comprises or consists of the substitution F228L of the mature polypeptide of SEQ ID NO: 2.

In another aspect, the variant comprises or consists of a substitution at a position corresponding to position F229. In another aspect, the amino acid at a position corresponding to position F229 is substituted with Ala, Arg, Asn, Asp, Cys, Gln, Glu, Gly, His, Ile, Leu, Lys, Met, Pro, Ser, Thr, Trp, Tyr, or Val, preferably with Leu. In another aspect, the variant comprises or consists of the substitution F229L of the mature polypeptide of SEQ ID NO: 2.

In another aspect, the variant comprises or consists of substitutions at positions corresponding to positions M94 and A144, such as those described above.

In another aspect, the variant comprises or consists of substitutions at positions corresponding to positions M94 and Y180, such as those described above.

In another aspect, the variant comprises or consists of substitutions at positions corresponding to positions M94 and W195, such as those described above.

In another aspect, the variant comprises or consists of substitutions at positions corresponding to positions M94 and Y215, such as those described above.

In another aspect, the variant comprises or consists of substitutions at positions corresponding to positions M94 and F224, such as those described above.

In another aspect, the variant comprises or consists of substitutions at positions corresponding to positions M94 and F228, such as those described above.

In another aspect, the variant comprises or consists of substitutions at positions corresponding to positions M94 and F229, such as those described above.

In another aspect, the variant comprises or consists of substitutions at positions corresponding to positions A144 and Y180, such as those described above.

In another aspect, the variant comprises or consists of substitutions at positions corresponding to positions A144 and W195, such as those described above.

In another aspect, the variant comprises or consists of substitutions at positions corresponding to positions A144 and Y215, such as those described above.

In another aspect, the variant comprises or consists of substitutions at positions corresponding to positions A144 and F224, such as those described above.

In another aspect, the variant comprises or consists of substitutions at positions corresponding to positions A144 and F228, such as those described above.

In another aspect, the variant comprises or consists of substitutions at positions corresponding to positions A144 and F229, such as those described above.

In another aspect, the variant comprises or consists of substitutions at positions corresponding to positions Y180 and W195, such as those described above.

In another aspect, the variant comprises or consists of substitutions at positions corresponding to positions Y180 and Y215, such as those described above.

In another aspect, the variant comprises or consists of substitutions at positions corresponding to positions Y180 and F224, such as those described above.

In another aspect, the variant comprises or consists of substitutions at positions corresponding to positions Y180 and F228, such as those described above.

In another aspect, the variant comprises or consists of substitutions at positions corresponding to positions Y180 and F229, such as those described above.

In another aspect, the variant comprises or consists of substitutions at positions corresponding to positions W195 and Y215, such as those described above.

In another aspect, the variant comprises or consists of substitutions at positions corresponding to positions W195 and F224, such as those described above.

In another aspect, the variant comprises or consists of substitutions at positions corresponding to positions W195 and F228, such as those described above.

In another aspect, the variant comprises or consists of substitutions at positions corresponding to positions W195 and F229, such as those described above.

In another aspect, the variant comprises or consists of substitutions at positions corresponding to positions Y215 and F224, such as those described above.

In another aspect, the variant comprises or consists of substitutions at positions corresponding to positions Y215 and F228, such as those described above.

In another aspect, the variant comprises or consists of substitutions at positions corresponding to positions Y215 and F229, such as those described above.

In another aspect, the variant comprises or consists of substitutions at positions corresponding to positions F224 and F228, such as those described above.

In another aspect, the variant comprises or consists of substitutions at positions corresponding to positions F224 and F229, such as those described above.

In another aspect, the variant comprises or consists of substitutions at positions corresponding to positions F228 and F229, such as those described above.

In another aspect, the variant comprises or consists of substitutions at positions corresponding to positions M94, A144, and Y180, such as those described above.

In another aspect, the variant comprises or consists of substitutions at positions corresponding to positions M94, A144, and W195, such as those described above.

In another aspect, the variant comprises or consists of substitutions at positions corresponding to positions M94, A144, and Y215, such as those described above.

In another aspect, the variant comprises or consists of substitutions at positions corresponding to positions M94, A144, and F224, such as those described above.

In another aspect, the variant comprises or consists of substitutions at positions corresponding to positions M94, A144, and F228, such as those described above.

In another aspect, the variant comprises or consists of substitutions at positions corresponding to positions M94, A144, and F229, such as those described above.

In another aspect, the variant comprises or consists of substitutions at positions corresponding to positions M94, Y180, and W195, such as those described above.

In another aspect, the variant comprises or consists of substitutions at positions corresponding to positions M94, Y180, and Y215, such as those described above.

In another aspect, the variant comprises or consists of substitutions at positions corresponding to positions M94, Y180, and F224, such as those described above.

In another aspect, the variant comprises or consists of substitutions at positions corresponding to positions M94, Y180, and F228, such as those described above.

In another aspect, the variant comprises or consists of substitutions at positions corresponding to positions M94, Y180, and F229, such as those described above.

In another aspect, the variant comprises or consists of substitutions at positions corresponding to positions M94, W195, and Y215, such as those described above.

In another aspect, the variant comprises or consists of substitutions at positions corresponding to positions M94, W195, and F224, such as those described above.

In another aspect, the variant comprises or consists of substitutions at positions corresponding to positions M94, W195, and F228, such as those described above.

In another aspect, the variant comprises or consists of substitutions at positions corresponding to positions M94, W195, and F229, such as those described above.

In another aspect, the variant comprises or consists of substitutions at positions corresponding to positions M94, Y215, and F224, such as those described above.

In another aspect, the variant comprises or consists of substitutions at positions corresponding to positions M94, Y215, and F228, such as those described above.

In another aspect, the variant comprises or consists of substitutions at positions corresponding to positions M94, Y215, and F229, such as those described above.

In another aspect, the variant comprises or consists of substitutions at positions corresponding to positions M94, F224, and F228, such as those described above.

In another aspect, the variant comprises or consists of substitutions at positions corresponding to positions M94, F224, and F229, such as those described above.

In another aspect, the variant comprises or consists of substitutions at positions corresponding to positions M94, F228, and F229, such as those described above.

In another aspect, the variant comprises or consists of substitutions at positions corresponding to positions A144, Y180, and W195, such as those described above.

In another aspect, the variant comprises or consists of substitutions at positions corresponding to positions A144, Y180, and Y215, such as those described above.

In another aspect, the variant comprises or consists of substitutions at positions corresponding to positions A144, Y180, and F224, such as those described above.

In another aspect, the variant comprises or consists of substitutions at positions corresponding to positions A144, Y180, and F228, such as those described above.

In another aspect, the variant comprises or consists of substitutions at positions corresponding to positions A144, Y180, and F229, such as those described above.

In another aspect, the variant comprises or consists of substitutions at positions corresponding to positions A144, W195, and Y215, such as those described above.

In another aspect, the variant comprises or consists of substitutions at positions corresponding to positions A144, W195, and F224, such as those described above.

In another aspect, the variant comprises or consists of substitutions at positions corresponding to positions A144, W195, and F228, such as those described above.

In another aspect, the variant comprises or consists of substitutions at positions corresponding to positions A144, W195, and F229, such as those described above.

In another aspect, the variant comprises or consists of substitutions at positions corresponding to positions A144, Y215, and F224, such as those described above.

In another aspect, the variant comprises or consists of substitutions at positions corresponding to positions A144, Y215, and F228, such as those described above.

In another aspect, the variant comprises or consists of substitutions at positions corresponding to positions A144, Y215, and F229, such as those described above.

In another aspect, the variant comprises or consists of substitutions at positions corresponding to positions A144, F224, and F228, such as those described above.

In another aspect, the variant comprises or consists of substitutions at positions corresponding to positions A144, F224, and F229, such as those described above.

In another aspect, the variant comprises or consists of substitutions at positions corresponding to positions A144, F228, and F229, such as those described above.

In another aspect, the variant comprises or consists of substitutions at positions corresponding to positions Y180, W195, and Y215, such as those described above.

In another aspect, the variant comprises or consists of substitutions at positions corresponding to positions Y180, W195, and F224, such as those described above.

In another aspect, the variant comprises or consists of substitutions at positions corresponding to positions Y180, W195, and F228, such as those described above.

In another aspect, the variant comprises or consists of substitutions at positions corresponding to positions Y180, W195, and F229, such as those described above.

In another aspect, the variant comprises or consists of substitutions at positions corresponding to positions Y180, Y215, and F224, such as those described above.

In another aspect, the variant comprises or consists of substitutions at positions corresponding to positions Y180, Y215, and F228, such as those described above.

In another aspect, the variant comprises or consists of substitutions at positions corresponding to positions Y180, Y215, and F229, such as those described above.

In another aspect, the variant comprises or consists of substitutions at positions corresponding to positions Y180, F224, and F228, such as those described above.

In another aspect, the variant comprises or consists of substitutions at positions corresponding to positions Y180, F224, and F229, such as those described above.

In another aspect, the variant comprises or consists of substitutions at positions corresponding to positions Y180, F228, and F229, such as those described above.

In another aspect, the variant comprises or consists of substitutions at positions corresponding to positions W195, Y215, and F224, such as those described above.

In another aspect, the variant comprises or consists of substitutions at positions corresponding to positions W195, Y215, and F228, such as those described above.

In another aspect, the variant comprises or consists of substitutions at positions corresponding to positions W195, Y215, and F229, such as those described above.

In another aspect, the variant comprises or consists of substitutions at positions corresponding to positions W195, F224, and F228, such as those described above.

In another aspect, the variant comprises or consists of substitutions at positions corresponding to positions W195, F224, and F229, such as those described above.

In another aspect, the variant comprises or consists of substitutions at positions corresponding to positions W195, F228, and F229, such as those described above.

In another aspect, the variant comprises or consists of substitutions at positions corresponding to positions Y215, F224, and F228, such as those described above.

In another aspect, the variant comprises or consists of substitutions at positions corresponding to positions Y215, F224, and F229, such as those described above.

In another aspect, the variant comprises or consists of substitutions at positions corresponding to positions Y215, F228, and F229, such as those described above.

In another aspect, the variant comprises or consists of substitutions at positions corresponding to positions F224, F228, and F229, such as those described above.

In another aspect, the variant comprises or consists of substitutions at positions corresponding to positions M94, A144, Y180, and W195, such as those described above.

In another aspect, the variant comprises or consists of substitutions at positions corresponding to positions M94, A144, Y180, and Y215, such as those described above.

In another aspect, the variant comprises or consists of substitutions at positions corresponding to positions M94, A144, Y180, and F224, such as those described above.

In another aspect, the variant comprises or consists of substitutions at positions corresponding to positions M94, A144, Y180, and F228, such as those described above.

In another aspect, the variant comprises or consists of substitutions at positions corresponding to positions M94, A144, Y180, and F229, such as those described above.

In another aspect, the variant comprises or consists of substitutions at positions corresponding to positions M94, A144, W195, and Y215, such as those described above.

In another aspect, the variant comprises or consists of substitutions at positions corresponding to positions M94, A144, W195, and F224, such as those described above.

In another aspect, the variant comprises or consists of substitutions at positions corresponding to positions M94, A144, W195, and F228, such as those described above.

In another aspect, the variant comprises or consists of substitutions at positions corresponding to positions M94, A144, W195, and F229, such as those described above.

In another aspect, the variant comprises or consists of substitutions at positions corresponding to positions M94, A144, Y215, and F224, such as those described above.

In another aspect, the variant comprises or consists of substitutions at positions corresponding to positions M94, A144, Y215, and F228, such as those described above.

In another aspect, the variant comprises or consists of substitutions at positions corresponding to positions M94, A144, Y215, and F229, such as those described above.

In another aspect, the variant comprises or consists of substitutions at positions corresponding to positions M94, A144, F224, and F228, such as those described above.

In another aspect, the variant comprises or consists of substitutions at positions corresponding to positions M94, A144, F224, and F229, such as those described above.

In another aspect, the variant comprises or consists of substitutions at positions corresponding to positions M94, A144, F228, and F229, such as those described above.

In another aspect, the variant comprises or consists of substitutions at positions corresponding to positions M94, Y180, W195, and Y215, such as those described above.

In another aspect, the variant comprises or consists of substitutions at positions corresponding to positions M94, Y180, W195, and F224, such as those described above.

In another aspect, the variant comprises or consists of substitutions at positions corresponding to positions M94, Y180, W195, and F228, such as those described above.

In another aspect, the variant comprises or consists of substitutions at positions corresponding to positions M94, Y180, W195, and F229, such as those described above.

In another aspect, the variant comprises or consists of substitutions at positions corresponding to positions M94, Y180, Y215, and F224, such as those described above.

In another aspect, the variant comprises or consists of substitutions at positions corresponding to positions M94, Y180, Y215, and F228, such as those described above.

In another aspect, the variant comprises or consists of substitutions at positions corresponding to positions M94, Y180, Y215, and F229, such as those described above.

In another aspect, the variant comprises or consists of substitutions at positions corresponding to positions M94, Y180, F224, and F228, such as those described above.

In another aspect, the variant comprises or consists of substitutions at positions corresponding to positions M94, Y180, F224, and F229, such as those described above.

In another aspect, the variant comprises or consists of substitutions at positions corresponding to positions M94, Y180, F228, and F229, such as those described above.

In another aspect, the variant comprises or consists of substitutions at positions corresponding to positions M94, W195, Y215, and F224, such as those described above.

In another aspect, the variant comprises or consists of substitutions at positions corresponding to positions M94, W195, Y215, and F228, such as those described above.

In another aspect, the variant comprises or consists of substitutions at positions corresponding to positions M94, W195, Y215, and F229, such as those described above.

In another aspect, the variant comprises or consists of substitutions at positions corresponding to positions M94, W195, F224, and F228, such as those described above.

In another aspect, the variant comprises or consists of substitutions at positions corresponding to positions M94, W195, F224, and F229, such as those described above.

In another aspect, the variant comprises or consists of substitutions at positions corresponding to positions M94, W195, F228, and F229, such as those described above.

In another aspect, the variant comprises or consists of substitutions at positions corresponding to positions M94, Y215, F224, and F228, such as those described above.

In another aspect, the variant comprises or consists of substitutions at positions corresponding to positions M94, Y215, F224, and F229, such as those described above.

In another aspect, the variant comprises or consists of substitutions at positions corresponding to positions M94, Y215, F228, and F229, such as those described above.

In another aspect, the variant comprises or consists of substitutions at positions corresponding to positions M94, F224, F228, and F229, such as those described above.

In another aspect, the variant comprises or consists of substitutions at positions corresponding to positions A144, Y180, W195, and Y215, such as those described above.

In another aspect, the variant comprises or consists of substitutions at positions corresponding to positions A144, Y180, W195, and F224, such as those described above.

In another aspect, the variant comprises or consists of substitutions at positions corresponding to positions A144, Y180, W195, and F228, such as those described above.

In another aspect, the variant comprises or consists of substitutions at positions corresponding to positions A144, Y180, W195, and F229, such as those described above.

In another aspect, the variant comprises or consists of substitutions at positions corresponding to positions A144, Y180, Y215, and F224, such as those described above.

In another aspect, the variant comprises or consists of substitutions at positions corresponding to positions A144, Y180, Y215, and F228, such as those described above.

In another aspect, the variant comprises or consists of substitutions at positions corresponding to positions A144, Y180, Y215, and F229, such as those described above.

In another aspect, the variant comprises or consists of substitutions at positions corresponding to positions A144, Y180, F224, and F228, such as those described above.

In another aspect, the variant comprises or consists of substitutions at positions corresponding to positions A144, Y180, F224, and F229, such as those described above.

In another aspect, the variant comprises or consists of substitutions at positions corresponding to positions A144, Y180, F228, and F229, such as those described above.

In another aspect, the variant comprises or consists of substitutions at positions corresponding to positions A144, W195, Y215, and F224, such as those described above.

In another aspect, the variant comprises or consists of substitutions at positions corresponding to positions A144, W195, Y215, and F228, such as those described above.

In another aspect, the variant comprises or consists of substitutions at positions corresponding to positions A144, W195, Y215, and F229, such as those described above.

In another aspect, the variant comprises or consists of substitutions at positions corresponding to positions A144, W195, F224, and F228, such as those described above.

In another aspect, the variant comprises or consists of substitutions at positions corresponding to positions A144, W195, F224, and F229, such as those described above.

In another aspect, the variant comprises or consists of substitutions at positions corresponding to positions A144, W195, F228, and F229, such as those described above.

In another aspect, the variant comprises or consists of substitutions at positions corresponding to positions A144, Y215, F224, and F228, such as those described above.

In another aspect, the variant comprises or consists of substitutions at positions corresponding to positions A144, Y215, F224, and F229, such as those described above.

In another aspect, the variant comprises or consists of substitutions at positions corresponding to positions A144, Y215, F228, and F229, such as those described above.

In another aspect, the variant comprises or consists of substitutions at positions corresponding to positions A144, F224, F228, and F229, such as those described above.

In another aspect, the variant comprises or consists of substitutions at positions corresponding to positions Y180, W195, Y215, and F224, such as those described above.

In another aspect, the variant comprises or consists of substitutions at positions corresponding to positions Y180, W195, Y215, and F228, such as those described above.

In another aspect, the variant comprises or consists of substitutions at positions corresponding to positions Y180, W195, Y215, and F229, such as those described above.

In another aspect, the variant comprises or consists of substitutions at positions corresponding to positions Y180, W195, F224, and F228, such as those described above.

In another aspect, the variant comprises or consists of substitutions at positions corresponding to positions Y180, W195, F224, and F229, such as those described above.

In another aspect, the variant comprises or consists of substitutions at positions corresponding to positions Y180, W195, F228, and F229, such as those described above.

In another aspect, the variant comprises or consists of substitutions at positions corresponding to positions Y180, Y215, F224, and F228, such as those described above.

In another aspect, the variant comprises or consists of substitutions at positions corresponding to positions Y180, Y215, F224, and F229, such as those described above.

In another aspect, the variant comprises or consists of substitutions at positions corresponding to positions Y180, Y215, F228, and F229, such as those described above.

In another aspect, the variant comprises or consists of substitutions at positions corresponding to positions Y180, F224, F228, and F229, such as those described above.

In another aspect, the variant comprises or consists of substitutions at positions corresponding to positions W195, Y215, F224, and F228, such as those described above.

In another aspect, the variant comprises or consists of substitutions at positions corresponding to positions W195, Y215, F224, and F229, such as those described above.

In another aspect, the variant comprises or consists of substitutions at positions corresponding to positions W195, Y215, F228, and F229, such as those described above.

In another aspect, the variant comprises or consists of substitutions at positions corresponding to positions W195, F224, F228, and F229, such as those described above.

In another aspect, the variant comprises or consists of substitutions at positions corresponding to positions Y215, F224, F228, and F229, such as those described above.

In another aspect, the variant comprises or consists of substitutions at positions corresponding to positions M94, A144, Y180, W195, and Y215, such as those described above.

In another aspect, the variant comprises or consists of substitutions at positions corresponding to positions M94, A144, Y180, W195, and F224, such as those described above.

In another aspect, the variant comprises or consists of substitutions at positions corresponding to positions M94, A144, Y180, W195, and F228, such as those described above.

In another aspect, the variant comprises or consists of substitutions at positions corresponding to positions M94, A144, Y180, W195, and F229, such as those described above.

In another aspect, the variant comprises or consists of substitutions at positions corresponding to positions M94, A144, Y180, Y215, and F224, such as those described above.

In another aspect, the variant comprises or consists of substitutions at positions corresponding to positions M94, A144, Y180, Y215, and F228, such as those described above.

In another aspect, the variant comprises or consists of substitutions at positions corresponding to positions M94, A144, Y180, Y215, and F229, such as those described above.

In another aspect, the variant comprises or consists of substitutions at positions corresponding to positions M94, A144, Y180, F224, and F228, such as those described above.

In another aspect, the variant comprises or consists of substitutions at positions corresponding to positions M94, A144, Y180, F224, and F229, such as those described above.

In another aspect, the variant comprises or consists of substitutions at positions corresponding to positions M94, A144, Y180, F228, and F229, such as those described above.

In another aspect, the variant comprises or consists of substitutions at positions corresponding to positions M94, A144, W195, Y215, and F224, such as those described above.

In another aspect, the variant comprises or consists of substitutions at positions corresponding to positions M94, A144, W195, Y215, and F228, such as those described above.

In another aspect, the variant comprises or consists of substitutions at positions corresponding to positions M94, A144, W195, Y215, and F229, such as those described above.

In another aspect, the variant comprises or consists of substitutions at positions corresponding to positions M94, A144, W195, F224, and F228, such as those described above.

In another aspect, the variant comprises or consists of substitutions at positions corresponding to positions M94, A144, W195, F224, and F229, such as those described above.

In another aspect, the variant comprises or consists of substitutions at positions corresponding to positions M94, A144, W195, F228, and F229, such as those described above.

In another aspect, the variant comprises or consists of substitutions at positions corresponding to positions M94, A144, Y215, F224, and F228, such as those described above.

In another aspect, the variant comprises or consists of substitutions at positions corresponding to positions M94, A144, Y215, F224, and F229, such as those described above.

In another aspect, the variant comprises or consists of substitutions at positions corresponding to positions M94, A144, Y215, F228, and F229, such as those described above.

In another aspect, the variant comprises or consists of substitutions at positions corresponding to positions M94, A144, F224, F228, and F229, such as those described above.

In another aspect, the variant comprises or consists of substitutions at positions corresponding to positions M94, Y180, W195, Y215, and F224, such as those described above.

In another aspect, the variant comprises or consists of substitutions at positions corresponding to positions M94, Y180, W195, Y215, and F228, such as those described above.

In another aspect, the variant comprises or consists of substitutions at positions corresponding to positions M94, Y180, W195, Y215, and F229, such as those described above.

In another aspect, the variant comprises or consists of substitutions at positions corresponding to positions M94, Y180, W195, F224, and F228, such as those described above.

In another aspect, the variant comprises or consists of substitutions at positions corresponding to positions M94, Y180, W195, F224, and F229, such as those described above.

In another aspect, the variant comprises or consists of substitutions at positions corresponding to positions M94, Y180, W195, F228, and F229, such as those described above.

In another aspect, the variant comprises or consists of substitutions at positions corresponding to positions M94, Y180, Y215, F224, and F228, such as those described above.

In another aspect, the variant comprises or consists of substitutions at positions corresponding to positions M94, Y180, Y215, F224, and F229, such as those described above.

In another aspect, the variant comprises or consists of substitutions at positions corresponding to positions M94, Y180, Y215, F228, and F229, such as those described above.

In another aspect, the variant comprises or consists of substitutions at positions corresponding to positions M94, Y180, F224, F228, and F229, such as those described above.

In another aspect, the variant comprises or consists of substitutions at positions corresponding to positions M94, W195, Y215, F224, and F228, such as those described above.

In another aspect, the variant comprises or consists of substitutions at positions corresponding to positions M94, W195, Y215, F224, and F229, such as those described above.

In another aspect, the variant comprises or consists of substitutions at positions corresponding to positions M94, W195, Y215, F228, and F229, such as those described above.

In another aspect, the variant comprises or consists of substitutions at positions corresponding to positions M94, W195, F224, F228, and F229, such as those described above.

In another aspect, the variant comprises or consists of substitutions at positions corresponding to positions M94, Y215, F224, F228, and F229, such as those described above.

In another aspect, the variant comprises or consists of substitutions at positions corresponding to positions A144, Y180, W195, Y215, and F224, such as those described above.

In another aspect, the variant comprises or consists of substitutions at positions corresponding to positions A144, Y180, W195, Y215, and F228, such as those described above.

In another aspect, the variant comprises or consists of substitutions at positions corresponding to positions A144, Y180, W195, Y215, and F229, such as those described above.

In another aspect, the variant comprises or consists of substitutions at positions corresponding to positions A144, Y180, W195, F224, and F228, such as those described above.

In another aspect, the variant comprises or consists of substitutions at positions corresponding to positions A144, Y180, W195, F224, and F229, such as those described above.

In another aspect, the variant comprises or consists of substitutions at positions corresponding to positions A144, Y180, W195, F228, and F229, such as those described above.

In another aspect, the variant comprises or consists of substitutions at positions corresponding to positions A144, Y180, Y215, F224, and F228, such as those described above.

In another aspect, the variant comprises or consists of substitutions at positions corresponding to positions A144, Y180, Y215, F224, and F229, such as those described above.

In another aspect, the variant comprises or consists of substitutions at positions corresponding to positions A144, Y180, Y215, F228, and F229, such as those described above.

In another aspect, the variant comprises or consists of substitutions at positions corresponding to positions A144, Y180, F224, F228, and F229, such as those described above.

In another aspect, the variant comprises or consists of substitutions at positions corresponding to positions A144, W195, Y215, F224, and F228, such as those described above.

In another aspect, the variant comprises or consists of substitutions at positions corresponding to positions A144, W195, Y215, F224, and F229, such as those described above.

In another aspect, the variant comprises or consists of substitutions at positions corresponding to positions A144, W195, Y215, F228, and F229, such as those described above.

In another aspect, the variant comprises or consists of substitutions at positions corresponding to positions A144, W195, F224, F228, and F229, such as those described above.

In another aspect, the variant comprises or consists of substitutions at positions corresponding to positions A144, Y215, F224, F228, and F229, such as those described above.

In another aspect, the variant comprises or consists of substitutions at positions corresponding to positions Y180, W195, Y215, F224, and F228, such as those described above.

In another aspect, the variant comprises or consists of substitutions at positions corresponding to positions Y180, W195, Y215, F224, and F229, such as those described above.

In another aspect, the variant comprises or consists of substitutions at positions corresponding to positions Y180, W195, Y215, F228, and F229, such as those described above.

In another aspect, the variant comprises or consists of substitutions at positions corresponding to positions Y180, W195, F224, F228, and F229, such as those described above.

In another aspect, the variant comprises or consists of substitutions at positions corresponding to positions Y180, Y215, F224, F228, and F229, such as those described above.

In another aspect, the variant comprises or consists of substitutions at positions corresponding to positions W195, Y215, F224, F228, and F229, such as those described above.

In another aspect, the variant comprises or consists of substitutions at positions corresponding to positions M94, A144, Y180, W195, Y215, and F224, such as those described above.

In another aspect, the variant comprises or consists of substitutions at positions corresponding to positions M94, A144, Y180, W195, Y215, and F228, such as those described above.

In another aspect, the variant comprises or consists of substitutions at positions corresponding to positions M94, A144, Y180, W195, Y215, and F229, such as those described above.

In another aspect, the variant comprises or consists of substitutions at positions corresponding to positions M94, A144, Y180, W195, F224, and F228, such as those described above.

In another aspect, the variant comprises or consists of substitutions at positions corresponding to positions M94, A144, Y180, W195, F224, and F229, such as those described above.

In another aspect, the variant comprises or consists of substitutions at positions corresponding to positions M94, A144, Y180, W195, F228, and F229, such as those described above.

In another aspect, the variant comprises or consists of substitutions at positions corresponding to positions M94, A144, Y180, Y215, F224, and F228, such as those described above.

In another aspect, the variant comprises or consists of substitutions at positions corresponding to positions M94, A144, Y180, Y215, F224, and F229, such as those described above.

In another aspect, the variant comprises or consists of substitutions at positions corresponding to positions M94, A144, Y180, Y215, F228, and F229, such as those described above.

In another aspect, the variant comprises or consists of substitutions at positions corresponding to positions M94, A144, Y180, F224, F228, and F229, such as those described above.

In another aspect, the variant comprises or consists of substitutions at positions corresponding to positions M94, A144, W195, Y215, F224, and F228, such as those described above.

In another aspect, the variant comprises or consists of substitutions at positions corresponding to positions M94, A144, W195, Y215, F224, and F229, such as those described above.

In another aspect, the variant comprises or consists of substitutions at positions corresponding to positions M94, A144, W195, Y215, F228, and F229, such as those described above.

In another aspect, the variant comprises or consists of substitutions at positions corresponding to positions M94, A144, W195, F224, F228, and F229, such as those described above.

In another aspect, the variant comprises or consists of substitutions at positions corresponding to positions M94, A144, Y215, F224, F228, and F229, such as those described above.

In another aspect, the variant comprises or consists of substitutions at positions corresponding to positions M94, Y180, W195, Y215, F224, and F228, such as those described above.

In another aspect, the variant comprises or consists of substitutions at positions corresponding to positions M94, Y180, W195, Y215, F224, and F229, such as those described above.

In another aspect, the variant comprises or consists of substitutions at positions corresponding to positions M94, Y180, W195, Y215, F228, and F229, such as those described above.

In another aspect, the variant comprises or consists of substitutions at positions corresponding to positions M94, Y180, W195, F224, F228, and F229, such as those described above.

In another aspect, the variant comprises or consists of substitutions at positions corresponding to positions M94, Y180, Y215, F224, F228, and F229, such as those described above.

In another aspect, the variant comprises or consists of substitutions at positions corresponding to positions M94, W195, Y215, F224, F228, and F229, such as those described above.

In another aspect, the variant comprises or consists of substitutions at positions corresponding to positions A144, Y180, W195, Y215, F224, and F228, such as those described above.

In another aspect, the variant comprises or consists of substitutions at positions corresponding to positions A144, Y180, W195, Y215, F224, and F229, such as those described above.

In another aspect, the variant comprises or consists of substitutions at positions corresponding to positions A144, Y180, W195, Y215, F228, and F229, such as those described above.

In another aspect, the variant comprises or consists of substitutions at positions corresponding to positions A144, Y180, W195, F224, F228, and F229, such as those described above.

In another aspect, the variant comprises or consists of substitutions at positions corresponding to positions A144, Y180, Y215, F224, F228, and F229, such as those described above.

In another aspect, the variant comprises or consists of substitutions at positions corresponding to positions A144, W195, Y215, F224, F228, and F229, such as those described above.

In another aspect, the variant comprises or consists of substitutions at positions corresponding to positions Y180, W195, Y215, F224, F228, and F229, such as those described above.

In another aspect, the variant comprises or consists of substitutions at positions corresponding to positions M94, A144, Y180, W195, Y215, F224, and F228, such as those described above.

In another aspect, the variant comprises or consists of substitutions at positions corresponding to positions M94, A144, Y180, W195, Y215, F224, and F229, such as those described above.

In another aspect, the variant comprises or consists of substitutions at positions corresponding to positions M94, A144, Y180, W195, Y215, F228, and F229, such as those described above.

In another aspect, the variant comprises or consists of substitutions at positions corresponding to positions M94, A144, Y180, W195, F224, F228, and F229, such as those described above.

In another aspect, the variant comprises or consists of substitutions at positions corresponding to positions M94, A144, Y180, Y215, F224, F228, and F229, such as those described above.

In another aspect, the variant comprises or consists of substitutions at positions corresponding to positions M94, A144, W195, Y215, F224, F228, and F229, such as those described above.

In another aspect, the variant comprises or consists of substitutions at positions corresponding to positions M94, Y180, W195, Y215, F224, F228, and F229, such as those described above.

In another aspect, the variant comprises or consists of substitutions at positions corresponding to positions A144, Y180, W195, Y215, F224, F228, and F229, such as those described above.

In another aspect, the variant comprises or consists of substitutions at positions corresponding to positions M94, A144, Y180, W195, Y215, F224, F228, and F229, such as those described above.

In another aspect, the variant comprises or consists of one or more (e.g., several) substitutions selected from the group consisting of E16D, Y18I, P28A, P31A, W38F, R50E, Y72F, F92L, M94F, I98L, I98V, T100K, H102R, C103S, Y104F, H107F, L114I, A144R, F146L, M152L, F163C, Q167E, Y180F, Y180F, T188A, W195F, M202L, Y215F, F216L, S222A, F224G, F224L, F228L, F229L, M246L, F253L, H256S, Y258F, Y281F, Y287R, F308G, L317N, T319S, S345G, F346V, P347*, G348*, S349A, and G350A; preferably M94F, A144R, Y180F, W195F, Y215F, F224L, F224G, F228L, and F229L.

In another aspect, the variant comprises or consists of the substitutions selected from the group consisting of E16D, Y18I, P28A, P31A, W38F, R50E, Y72F, F92L, M94F, I98L, I98V, T100K, H102R, C103S, Y104F, H107F, L114I, A144R, F146L, M152L, F163C, Q167E, Y180F, Y180F, T188A, W195F, M202L, Y215F, F216L, S222A, F224G, F224L, F228L, F229L, M246L, F253L, H256S, Y258F, Y281F, Y287R, F308G, L317N, T319S, S345G, F346V, P347*, G348*, S349A, and G350A; preferably M94F, A144R, Y180F, W195F, Y215F, F224L, F224G, F228L, and F229L of the mature polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 2 which has peroxygenase activity, and further the variant has improved oxidation stability compared to the mature peroxygenase of SEQ ID NO: 2.

In another aspect, the variant comprises or consists of the substitutions selected from the group consisting of M94F, A144R, Y180F, W195F, Y215F, F224L, F224G, F228L, and F229L of the mature polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 2 which has peroxygenase activity, and further the variant has reduced catalase activity compared to the mature peroxygenase of SEQ ID NO: 2.

In another aspect, the variant comprises or consists of the substitutions selected from the group consisting of M94F, A144R, Y180F, W195F, Y215F, F224L, F224G, F228L, and F229L of the mature polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 2 which has peroxygenase activity, and further the variant has reduced peroxidase activity compared to the mature peroxygenase of SEQ ID NO: 2.

In another aspect, the variant comprises or consists of the substitutions selected from the group consisting of M94F, A144R, Y180F, W195F, Y215F, F224L, F224G, F228L, and F229L of the mature polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 2 which has peroxygenase activity, and further the variant has improved activity on veratryl alcohol compared to the mature peroxygenase of SEQ ID NO: 2.

In another aspect, the variant comprises or consists of the substitutions selected from the group consisting of E16D, W38F, Y104F, Y180F, S222A, F228L, F229L, and H256S of the mature polypeptide of SEQ ID NO: 2, or of a polypeptide having at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to the mature polypeptide of SEQ ID NO: 2 which has peroxygenase activity, and further the variant has improved activity on cyclohexane compared to the mature peroxygenase of SEQ ID NO: 2.

The variants may further comprise one or more additional substitutions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for peroxygenase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

In an embodiment, the variant has improved oxidation stability compared to the parent enzyme.

In an embodiment, the variant has improved storage stability compared to the parent enzyme.

In an embodiment, the variant has reduced catalase activity compared to the parent enzyme.

In an embodiment, the variant has reduced peroxidase activity compared to the parent enzyme.

In an embodiment, the variant has improved activity on veratryl alcohol compared to the parent enzyme.

In an embodiment, the variant has improved activity on cyclohexane compared to the parent enzyme.

Parent Peroxygenases

The parent peroxygenase may be (a) a polypeptide having at least 60% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, or (ii) the full-length complement of (i); or (c) a polypeptide encoded by a polynucleotide having at least 60% sequence identity to the mature polypeptide coding sequence of SEQ ID NO: 1.

In an aspect, the parent has a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have peroxygenase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2.

In another embodiment, the parent is an allelic variant of the mature polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify 2 and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a *Coprinopsis* peroxygenase, such as a *Coprinopsis acuminata*, *Coprinopsis atramentaria*, *Coprinopsis babosiae*, *Coprinopsis cinerea*, *Coprinopsis cinereofloccosa*, *Coprinopsis cothurnata*, *Coprinopsis echinospora*, *Coprinopsis episcopalis*, *Coprinopsis erythrocephala*, *Coprinopsis friesii*, *Coprinopsis fusispora*, *Coprinopsis gonophylla*, *Coprinopsis jonesii*, *Coprinopsis kubickae*, *Coprinopsis laanii*, *Coprinopsis lagopides*, *Coprinopsis lagopus*, *Coprinopsis macrocephala*, *Coprinopsis martinii*, *Coprinopsis narcotica*, *Coprinopsis nivea*, *Coprinopsis pachyderma*, *Coprinopsis phaeospora*, *Coprinopsis picacea*, *Coprinopsis pseudonivea*, *Coprinopsis stangliana*, *Coprinopsis stercorea*, *Coprinopsis tectispora*, *Coprinopsis trispora*, *Coprinopsis urticicola*, *Coprinopsis variegata*, or *Coprinopsis villosa* peroxygenase.

In another aspect, the parent is a *Coprinopsis cinerea* peroxygenase, e.g., the peroxygenase of SEQ ID NO: 2, or the mature polypeptide thereof.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having peroxygenase activity, comprising: (a) introducing into a parent peroxygenase a substitution at one or more (e.g., several) positions corresponding to positions E16, Y18, P28, P31, W38, R50, Y72, F92, M94, I98, T100, H102, C103, Y104, H107, L114, A144, F146, M152, F163, Q167, Y180, T188, W195, M202, Y215, F216, S222, F224, F228, F229, M246, F253, H256, Y258, Y281, Y287, F308, L317, T319, S345, F346, P347, G348, S349, and G350; preferably M94, A144, Y180, W195, Y215, F224, F228, and F229 of the mature polypeptide of SEQ ID NO: 2, wherein the variant has peroxygenase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Sac-*

*charomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces.* Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma.*

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi,* 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor,*

*Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions

The peroxygenase polypeptides of the invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention as described herein.

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art.

The detergent additive as well as the detergent composition may comprise one or more additional enzymes such as a protease, lipase, cutinase, amylase, carbohydrase, cellulase, pectinase, mannanase, arabinase, galactanase, xylanase, oxidase, e.g., a laccase, and/or peroxidase.

The polypeptide of the present invention may be added to a detergent composition in an amount corresponding to 0.001-100 mg of protein, such as 0.01-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

Methods and Uses

The peroxygenase polypeptides of the invention may be used for site specific hydroxylation in position 2 or position 3 of an aliphatic hydrocarbon. The aliphatic hydrocarbon must include a chain of at least 3 carbons, and either (one or more) end of the aliphatic hydrocarbon may be used as the starting point to determine which carbon is in position 2 or 3. The aliphatic hydrocarbon must have at least one hydrogen attached to the carbon (which is hydroxylated) in position 2 or 3. In a preferred embodiment, the carbon in position 2 or 3, which is hydroxylated with the peroxygenase, is unsubstituted (before the hydroxylation is carried out).

Accordingly, in a first aspect, the present invention provides a method for hydroxylation in position 2 or 3 of either end (one or more ends) of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a polypeptide having peroxygenase activity of the invention.

The method of the invention may be used for a variety of purposes, like bulk chemical synthesis (biocatalysis), increasing aqueous solubility of aliphatic hydrocarbons, bioremediation, and modification of the characteristics of food products.

The method of the invention may also be used for a number of industrial processes in which said hydroxylation reactions are beneficial. An example of such use is in the manufacture of pulp and paper products where alkanes and other relevant aliphatic hydrocarbons that are present in the wood (resin) can result in depositioning problems in the pulp and paper manufacturing process. These hydrophobic compounds are the precursors of the so-called pitch deposits within the pulp and paper manufacturing processes. Pitch deposition results in low quality pulp, and can cause the shutdown of pulp mill operations. Specific issues related to pulps with high extractives content include runnability problems, spots and holes in the paper, and sheet breaks. Treatment with peroxygenase can increase the solubility of said compounds and thereby mitigate problems.

Yet another use of the method of the invention is in i.e. oil or coal refineries where the peroxygenase catalyzed hydroxylation can be used to modify the solubility, viscosity and/or combustion characteristics of hydrocarbons. Specifically the treatment can lead to changes in the smoke point, the kindling point, the fire point and the boiling point of the hydrocarbons subjected to the treatment.

In the synthesis of bulk chemicals, agro chemicals (incl. pesticides), specialty chemicals and pharmaceuticals the method of the invention may obviously be relevant in terms of selectively introducing hydroxy groups in the substrates thereby affecting the solubility of the modified compound. Furthermore, the selective hydroxylation provides a site for further modification by methods known in the art of organic chemical synthesis and chemo-enzymatic synthesis.

Natural gas is extensively processed to remove higher alkanes. Hydroxylation of such higher alkanes may be used to improve water solubility, and thus facilitate removal of the higher alkanes by washing the natural gas stream. Removal may be performed at the well or during refining.

Hydroxylation of oil waste will significantly improve biodegradability and will be applicable both in connection with waste water treatment from refineries and bioremediation of contaminated ground or water In a second aspect, the present invention provides a method for hydroxylation in position 2 or 3 of the terminal end of an acyl group of a lipid, comprising contacting the lipid with hydrogen peroxide and a polypeptide having peroxygenase activity of the invention.

Hydroxylation of the acyl group of a lipid generally improves the aqueous solubility of the lipid. Accordingly, the method of the invention may be used to remove or reduce oil or lipid containing stains, like chocolate, from laundry, by contacting the laundry with a peroxygenase and a source of hydrogen peroxide, and optionally a surfactant.

In another aspect, the methods of the invention may be used to reduce unpleasant odors from laundry by contacting the laundry with a peroxygenase and a source of hydrogen peroxide, and optionally a surfactant. The method of the invention results in reduction of the amount of butanoic acid (butyric acid) in the laundry. Butanoic acid is formed during washing of laundry when certain animal fats and plant oils are hydrolyzed, e.g. by detergent lipase, to yield free fatty acids, including butanoic acid. Butanoic acid has an extremely unpleasant odor. The peroxygenase hydroxylates the butanoic acid to 2-hydroxybutyric acid (alpha-hydroxybutyric acid) or 3-hydroxybutyric acid (beta-hydroxybutyric acid).

The present invention also provides a method for site specific introduction of a hydroxy and/or an oxo (keto) group at the second or third carbon of at least two ends of an aliphatic hydrocarbon, using a peroxygenase polypeptide of the invention, and hydrogen peroxide.

The aliphatic hydrocarbon must include a chain of at least five carbons. The second and third carbons are determined by counting the carbon atoms from any end of the aliphatic hydrocarbon.

The aliphatic hydrocarbon must have at least one hydrogen attached to a carbon which is hydroxylated by attachment of a hydroxy group; and at least two hydrogens attached to a carbon when an oxo group is introduced. In a preferred embodiment, the second or third carbon is unsubstituted before being contacted with the peroxygenase.

According to the method of the invention, the hydroxy and/or oxo groups are introduced independently of each other at the (at least) two ends of the aliphatic hydrocarbon. Thus, a hydroxy group can be introduced at one end, at the same time as an oxo group is introduced at another (the other) end—and vice versa. Two hydroxy groups, or two oxo groups, or one hydroxy group and one oxo group, cannot be introduced at the same end of the aliphatic hydrocarbon. Some examples of combinations are shown in Example 1.

In the context of the present invention, "oxidation" means introduction of a hydroxy and/or an oxo group.

Accordingly, in a first aspect, the present invention provides a method for introducing a hydroxy and/or an oxo (keto) group at the second or third carbon of (at least) two ends of a substituted or unsubstituted, linear or branched, aliphatic hydrocarbon having at least five carbons and having at least one hydrogen attached to said second or third carbon, comprising contacting the aliphatic hydrocarbon with hydrogen peroxide and a polypeptide having peroxygenase activity of the invention.

In an embodiment, the aliphatic hydrocarbon is not n-hexane or n-decane.

In a preferred embodiment, the aliphatic hydrocarbon is oxidized to (converted to) a diol, by introduction of two hydroxy groups. More preferably, the two hydroxy groups are located at each end of a linear aliphatic hydrocarbon.

The method of the invention may be used for a variety of purposes, like bulk chemical synthesis (biocatalysis), increasing aqueous solubility of aliphatic hydrocarbons, bioremediation, and modification of the characteristics of food products.

The method of the invention may also be used for a number of industrial processes in which said oxidation reactions are beneficial. An example of such use is in the manufacture of pulp and paper products where alkanes and other relevant aliphatic hydrocarbons that are present in the wood (resin) can result in depositioning problems in the pulp and paper manufacturing process. These hydrophobic compounds are the precursors of the so-called pitch deposits within the pulp and paper manufacturing processes. Pitch deposition results in low quality pulp, and can cause the shutdown of pulp mill operations. Specific issues related to pulps with high extractives content include runnability problems, spots and holes in the paper, and sheet breaks. Treatment with peroxygenase can increase the solubility of said compounds and thereby mitigate problems.

Yet another use of the method of the invention is in, for example, oil or coal refineries where the peroxygenase catalyzed oxidation can be used to modify the solubility, viscosity and/or combustion characteristics of hydrocarbons. Specifically the treatment can lead to changes in the smoke point, the kindling point, the fire point and the boiling point of the hydrocarbons subjected to the treatment.

In the synthesis of bulk chemicals, agro chemicals (incl. pesticides), specialty chemicals and pharmaceuticals the method of the invention may obviously be relevant in terms of selectively introducing hydroxy groups in the substrates thereby affecting the solubility of the modified compound. Furthermore, the selective oxidation provides a site for further modification by methods known in the art of organic chemical synthesis and chemo-enzymatic synthesis.

Natural gas is extensively processed to remove higher alkanes. Oxidation of such higher alkanes may be used to improve water solubility, and thus facilitate removal of the higher alkanes by washing the natural gas stream. Removal may be performed at the well or during refining.

Oxidation, according to the invention, of oil waste will significantly improve biodegradability and will be applicable both in connection with waste water treatment from refineries and bioremediation of contaminated ground or water The methods of the invention may be carried out with an immobilized peroxygenase polypeptide of the invention.

The methods of the invention may be carried out in an aqueous solvent (reaction medium), various alcohols, ethers, other polar or non-polar solvents, or mixtures thereof. By studying the characteristics of the aliphatic hydrocarbon used in the methods of the invention, suitable examples of solvents are easily recognized by one skilled in the art. By raising or lowering the pressure at which the hydroxylation/oxidation is carried out, the solvent (reaction medium) and the aliphatic hydrocarbon can be maintained in a liquid phase at the reaction temperature.

The methods according to the invention may be carried out at a temperature between 0 and 90 degrees Celsius, preferably between 5 and 80 degrees Celsius, more preferably between 10 and 70 degrees Celsius, even more preferably between 15 and 60 degrees Celsius, most preferably between 20 and 50 degrees Celsius, and in particular between 20 and 40 degrees Celsius.

The methods of the invention may employ a treatment time of from 10 seconds to (at least) 24 hours, preferably from 1 minute to (at least) 12 hours, more preferably from 5 minutes to (at least) 6 hours, most preferably from 5 minutes to (at least) 3 hours, and in particular from 5 minutes to (at least) 1 hour.

Diols (di-hydroxy aliphatic hydrocarbons) produced by the method of the invention may be used for producing polyurethan. Polyurethane is a polymer composed of a chain of organic units joined by carbamate (urethane) links. Polyurethane polymers are formed through step-growth polymerization, by reacting a monomer (with at least two isocyanate functional groups) with another monomer (with at least two hydroxyl groups) in the presence of a catalyst.

The present invention also provides a method for introducing an oxo (keto) group at the second or third carbon of a substituted or unsubstituted, linear or branched, aliphatic hydrocarbon having at least five carbons and having at least two hydrogens attached to said second or third carbon, comprising contacting the aliphatic hydrocarbon with hydrogen peroxide and a polypeptide having peroxygenase activity of the invention.

In an embodiment, the aliphatic hydrocarbon is not n-hexane or n-decane.

In yet another aspect, the present invention also provides a method for introducing a hydroxy or an oxo group at a terminal carbon of a linear or branched aliphatic hydrocarbon having at least five carbons, which is substituted with a carboxy group, comprising contacting the aliphatic hydrocarbon with hydrogen peroxide and a polypeptide having peroxygenase activity of the invention.

In an embodiment, the aliphatic hydrocarbon which is substituted with a carboxy group is a fatty acid; preferably butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, or docosahexaenoic acid.

In an embodiment, the aliphatic hydrocarbon which is substituted with a carboxy group, is not lauric acid or palmitic acid.

In yet another aspect, the present invention also provides a method for changing (oxidizing) a primary alcohol of a linear or branched aliphatic hydrocarbon having at least five carbons to the corresponding acid, comprising contacting the alcohol of an aliphatic hydrocarbon with hydrogen peroxide and a polypeptide having peroxygenase activity of the invention.

For example, pentanol may be changed (oxidized) to pentanoic acid (valeric acid), hexanol may be changed to hexanoic acid (caproic acid), heptanol may be changed to heptanoic acid (enanthic acid), octanol may be changed to octanoic acid (caprylic acid), nonanol may be changed to nonanoic acid (pelargonic acid), decanol may be changed to decanoic acid (capric acid), dodecanol may be changed to dodecanoic acid (lauric acid), tetradecanol may be changed to tetradecanoic acid (myristic acid), hexadecanol may be changed to hexadecanoic acid (palmitic acid), octadecanol may be changed to octadecanoic acid (stearic acid), and eicosanol may be changed to eicosanoic acid (arachidic acid).

The polypeptides having peroxygenase activity of the invention (peroxygenase polypeptides or peroxygenases) are used in the methods of the invention in an amount of 0.005-50 ppm (mg/l), or 0.01-40, 0.02-30, 0.03-25, 0.04-20, 0.05-15, 0.05-10, 0.05-5, 0.05-1, 0.05-0.8, 0.05-0.6, or 0.1-0.5 ppm. The amount of enzyme refers to mg of a well-defined enzyme preparation.

In the methods of the invention, the peroxygenase may be applied alone or together with an additional enzyme. The term "an additional enzyme" means at least one additional enzyme, e.g. one, two, three, four, five, six, seven, eight, nine, ten or even more additional enzymes.

The term "applied together with" (or "used together with") means that the additional enzyme may be applied in the same, or in another step of the method of the invention. The other process step may be upstream or downstream, as compared to the step in which the peroxygenase is used.

In particular embodiments the additional enzyme is an enzyme which has protease, lipase, xylanase, cutinase, oxidoreductase, cellulase, endoglucanase, amylase, mannanase, steryl esterase, and/or cholesterol esterase activity. Examples of oxidoreductase enzymes are enzymes with laccase, and/or peroxidase activity.

The term "a step" of a method means at least one step, and it could be one, two, three, four, five or even more method steps. In other words the peroxygenases of the invention may be applied in at least one method step, and the additional enzyme(s) may also be applied in at least one method step, which may be the same or a different method step as compared to the step where the peroxygenase is used.

The term "enzyme preparation" means a product containing at least one peroxygenase. The enzyme preparation may also comprise enzymes having other enzyme activities. In addition to the enzymatic activity, such a preparation preferably contains at least one adjuvant. Examples of adjuvants are buffers, polymers, surfactants and stabilizing agents.

Hydrogen Peroxide

The hydrogen peroxide required by the peroxygenase may be provided as an aqueous solution of hydrogen peroxide or a hydrogen peroxide precursor for in situ production of hydrogen peroxide. Any solid entity which liberates upon dissolution a peroxide which is useable by peroxygenase can serve as a source of hydrogen peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide, perborates and peroxycarboxylic acids or salts thereof.

Another source of hydrogen peroxide is a hydrogen peroxide generating enzyme system, such as an oxidase together with a substrate for the oxidase. Examples of combinations of oxidase and substrate comprise, but are not limited to, amino acid oxidase (see e.g. U.S. Pat. No. 6,248,575) and a suitable amino acid, glucose oxidase (see e.g. WO 95/29996) and glucose, lactate oxidase and lactate, galactose oxidase (see e.g. WO 00/50606) and galactose, and aldose oxidase (see e.g. WO 99/31990) and a suitable aldose.

By studying EC 1.1.3._, EC 1.2.3._, EC 1.4.3._, and EC 1.5.3._ or similar classes (under the International Union of Biochemistry), other examples of such combinations of oxidases and substrates are easily recognized by one skilled in the art.

Hydrogen peroxide or a source of hydrogen peroxide may be added at the beginning of or during the method of the invention, e.g. as one or more separate additions of hydrogen peroxide; or continuously as fed-batch addition. Typical amounts of hydrogen peroxide correspond to levels of from 0.001 mM to 25 mM, preferably to levels of from 0.005 mM to 5 mM, and particularly to levels of from 0.01 to 1 mM hydrogen peroxide. Hydrogen peroxide may also be used in an amount corresponding to levels of from 0.1 mM to 25 mM, preferably to levels of from 0.5 mM to 15 mM, more preferably to levels of from 1 mM to 10 mM, and most preferably to levels of from 2 mM to 8 mM hydrogen peroxide.

Aliphatic Hydrocarbons

The hydrocarbons, which are hydroxylated in the method of the invention, are aliphatic hydrocarbons having a chain of at least 3 carbons, and having a hydrogen attached to the carbon in position 2 or 3. Preferably, the aliphatic hydrocarbon is an alkane or an alkene; more preferably, the aliphatic hydrocarbon is an alkane, such as propane, butane, pentane, hexane, heptane, octane, nonane or decane, or isomers thereof.

The aliphatic hydrocarbons may be linear, branched or cyclic. Branched hydrocarbons correspond to isomers of linear hydrocarbons. In an embodiment, the aliphatic hydrocarbons are linear or branched.

The aliphatic hydrocarbons are substituted or unsubstituted. Preferably, the aliphatic hydrocarbons are unsubstituted, such as non-activated hydrocarbons.

When the aliphatic hydrocarbons are substituted (functional groups attached), the preferred substituents are halogen, hydroxyl, carboxyl, amino, nitro, cyano, thiol, sulphonyl, formyl, acetyl, methoxy, ethoxy, phenyl, benzyl, xylyl, carbamoyl and sulfamoyl; more preferred substituents are chloro, hydroxyl, carboxyl and sulphonyl; and most preferred substituents are chloro and carboxyl.

The aliphatic hydrocarbons may be substituted by up to 10 substituents, up to 8 substituents, up to 6 substituents, up to 4 substituents, up to 2 substituents, or by up to one substituent.

In a preferred embodiment, the aliphatic hydrocarbon is a fatty acid (the substituent is a carboxyl group). Examples of fatty acids include, but are not limited to, butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, and docosahexaenoic acid.

In a second aspect, the aliphatic hydrocarbon is an acyl group of a lipid, such as a monoglyceride, diglyceride, triglyceride, phospholipid or sphingolipid; and the hydroxylation takes place in position 2 or position 3 of the terminal end of the acyl group. The acyl group must have at least one hydrogen attached to the carbon in position 2 or 3 of the terminal end. The acyl group may be saturated or unsaturated, and optionally functional groups (substituents) may be attached. Examples of acyl groups include, but are not limited to, the acyl forms of butanoic acid (butyric acid), pentanoic acid (valeric acid), hexanoic acid (caproic acid), heptanoic acid (enanthic acid), octanoic acid (caprylic acid), nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), eicosanoic acid (arachidic acid), linoleic acid, linolenic acid, arachidonic acid, eicosapentaenoic acid, and docosahexaenoic acid.

Plants

The present invention also relates to plants, e.g., a transgenic plant, plant part, or plant cell, comprising a polynucleotide of the present invention so as to express and produce the variant in recoverable quantities. The variant may be recovered from the plant or plant part. Alternatively, the plant or plant part containing the variant may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca*, *Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing a variant may be constructed in accordance with methods known in the art. In short, the plant or plant cell is constructed by incorporating one or more expression constructs encoding a variant into the plant host genome or chloroplast genome and propagating the resulting modified plant or plant cell into a transgenic plant or plant cell.

The expression construct is conveniently a nucleic acid construct that comprises a polynucleotide encoding a variant operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the variant is desired to be expressed. For instance, the expression of the gene encoding a variant may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 121: 285-294; Christensen et al., 1992, *Plant Mol. Biol.* 18: 675-689; Zhang et al., 1991, *Plant Cell* 13: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a variant in the plant. For instance, the promoter enhancer element may be an intron that is placed between the promoter and the polynucleotide encoding a variant. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a variant can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a variant of the present invention comprising: (a) cultivating a transgenic plant or a plant cell comprising a polynucleotide encoding the variant under conditions conducive for production of the variant; and (b) recovering the variant.

The present invention is further described by the following examples that should not be construed as limiting the scope of the invention.

EXAMPLES

Chemicals used as buffers and substrates were commercial products of at least reagent grade. 'Wildtype' is the peroxygenase with the amino acid sequence shown as SEQ ID NO: 2. The amino acid sequence shown in SEQ ID NO: 2 is used to determine the corresponding amino acid residue in the peroxygenase variants used in the Examples below (see also 'Conventions for Designation of Variants' above).

Example 1

Cloning and Expression

A plasmid containing the gene encoding the polypeptide was constructed and transformed into a suitable host cell using standard methods known in the art (see e.g. WO 2009/109500). In this case, the vector used was pENI2516 (see also WO 2004/069872, Example 2), into which the parent peroxygenase encoding gene was cloned, using the filamentous fungus *Aspergillus oryzae* as host.

Fermentation was carried out as a batch fermentation using a constant medium temperature of 30° C. and a start volume of 0.2 liter pr. shake flask. The batch fermentation medium contained maltose syrup as carbon source, urea and yeast extract as nitrogen source and a mixture of trace metals, salts and protoporhyrin IX. The shake flasks were shaken with 200 rpm for app. 100 hours.

Example 2

Purification 500-800 mL fermentation was filtrated using Rapid-Flow Bottle Top Filter with a 0.2 μm aPES membrane. The volume of sample was reduced until 100-200 ml, avoiding protein precipitation, using ultra-filtration Sartorius Stedim Biotech SartoJet Pump with 10 kDa cut-off membrane. 5 mM sodium acetate (CH3COONa) buffer pH 5 was added until 1 L, and then the volume was again reduced to 100-200 mL using ultra-filtration. The same buffer was added for a second time until 1 L and volume was reduced to 100 mL using ultra-filtration. The sample was diluted until its conductivity matched the conductivity of 25 mM sodium acetate buffer pH 5. The volume of sample was reduced to 100 mL using ultra-filtration Sartorius Stedim Biotech SartoJet Pump with 10 kDa cut of membrane. 19 mL SP-sepharose column (ø 16 mm) provided by GE healthcare was used in ion exchange chromatography.

The column was equilibrated with 25 mM sodium acetate pH5 buffer. Flow rate was 10 mL/min. Sample was loaded with same flow rate 10 mL/min. 57 mL of starting buffer were passed over the column, and then a gradient 0-100% of 25 mM sodium acetate with 0.5 M NaCl buffer pH 5 buffer was applied with same flow rate.

The fractions with high absorbance at 280 nm were collected and analyzed with Polyacrylamide gel electrophoresis (SDS-PAGE). Novex® 4-20% Tris-Glycine Mini Gel 1.0 m and a Mark12 (200-116.3-97.4-66.3-55.4-36.5-31.0-21.5-14.4-6.0-3.5-2.5 kDa) were used in order to select the factions with the higher protein concentration between 36.5-55.4 kDa and pool them together.

Enzyme concentrations were determined from the absorbance at 420 nm using an estimated extinction coefficient of 106 $mM^{-1}$ $cm^{-1}$.

Example 3

Oxidation Stability

Concept: Variants with increased activity on 4-nitrobenzodioxole in high concentrations of hydrogen peroxide are considered to have improved oxidation stability.

The enzymatic activity for the oxidation of 4-nitrobenzodioxole to 4-nitrocatechol was monitored spectrophotometrically at 425 nm at the following conditions: 1 mM 4-nitrocatechol was reacted with 0.5 mM H2O2 in the presence of 0.002 mg EP/mL in 50 mM phosphate buffer, pH 6.5 with 10% v/v of acetonitrile. The reaction mixtures of 0.2 mL in volume were measured in a 96 well microtitre plate at room temperature on a SpectraMax S384plus microtitre plate reader (Molecular Devices LLC, Sunnyvale, Calif., USA). The end concentration of 4-nitrocatechol was determined after 5 minutes from the absorbance at 425 nm using 4-nitrocatechol for calibration. Blank samples without addition of enzyme or hydrogen peroxide were included. Improved oxidation stability was evaluated from the oxidation of 4-nitrobenzodioxole to 4-nitrocatechol using the same procedure with 5 mM hydrogen peroxide.

The best variants were selected using the following procedure: Low activity variants that formed less than 0.03 mM 4-nitrocatechol at 0.5 mM H2O2 were first removed from the data set. The variants were then sorted according to the NBD activity at 5 mM H2O2 relative to 0.5 mM and compared against the wildtype.

TABLE 1

Peroxygenase variants having improved oxidation stability.

| Peroxygenase variant (amino acid changes) | NBD activity at 0.5 mM H2O2 | NBD activity at 5 mM H2O2 | Ratio of NBD activity at 5/0.5 mM H2O2 |
|---|---|---|---|
| F146L + F228L + S345G + F346V + G348* + P347* + S349A + G350A | 0.02 | 0.06 | 3.46 |
| P31A + M94F + Y180F + F224L + F228L + F229L | 0.05 | 0.13 | 2.93 |
| Y180F + F224L + F228L + F229L | 0.06 | 0.14 | 2.45 |

TABLE 1-continued

Peroxygenase variants having improved oxidation stability.

| Peroxygenase variant (amino acid changes) | NBD activity at 0.5 mM H2O2 | NBD activity at 5 mM H2O2 | Ratio of NBD activity at 5/0.5 mM H2O2 |
|---|---|---|---|
| W38F + Y180F + S222A + F228L + F229L | 0.13 | 0.31 | 2.36 |
| W38F + Y180F + F224L + F228L + F229L | 0.04 | 0.09 | 2.16 |
| F228L + F308L + S345G + F346V + G348* + P347* + S349A + G350A | 0.10 | 0.20 | 2.02 |
| M94F + Y180F + F228L + F229L | 0.10 | 0.18 | 1.81 |
| A144R + Y180F | 0.12 | 0.21 | 1.77 |
| Y180F + F224L + F228L | 0.04 | 0.07 | 1.69 |
| F216L + F228L + S345G + F346V + G348* + P347* + S349A + G350A | 0.03 | 0.04 | 1.55 |
| M94F | 0.10 | 0.15 | 1.54 |
| A144R + Y180F + F224L + F228L | 0.05 | 0.08 | 1.52 |
| P28A + M94F + Y180F + F224L + F228L + F229L | 0.04 | 0.06 | 1.45 |
| Y215F | 0.14 | 0.19 | 1.39 |
| F228L + S345G + F346V + P347* + G348* + S349A + G350A | 0.08 | 0.10 | 1.17 |
| C103S + H102R + W38F + A144R + Y180F | 0.03 | 0.03 | 0.98 |
| Y72F | 0.13 | 0.11 | 0.88 |
| Y180F + F224L + F229L | 0.05 | 0.04 | 0.87 |
| F163C + F228L + S345G + F346V + G348* + P347* + S349A + G350A | 0.10 | 0.08 | 0.76 |
| A144R + F163C + Y180F + T188A + S345G + F346V + G348* + P347* + S349A + G350A | 0.04 | 0.03 | 0.73 |
| W38F + Y180F + F224L + F228L + F229L + Y258F | 0.03 | 0.02 | 0.73 |
| F229L | 0.13 | 0.09 | 0.72 |
| W38F + Y180F + F224L + F228L + F229L | 0.06 | 0.04 | 0.68 |
| F228L | 0.08 | 0.05 | 0.65 |
| A144R + Y180F + F228L + F229L | 0.10 | 0.06 | 0.64 |
| A144R + Y180F + T188A + F308L + S345G + F346V + G348* + P347* + S349A + G350A | 0.05 | 0.03 | 0.58 |
| A144R | 0.07 | 0.04 | 0.57 |
| M246L | 0.10 | 0.05 | 0.55 |
| E16D | 0.07 | 0.04 | 0.51 |
| A144R + Y180F + S345G + F346V + G348* + P347* + S349A + G350A | 0.06 | 0.03 | 0.51 |
| F92L | 0.04 | 0.02 | 0.50 |
| I98L | 0.05 | 0.02 | 0.49 |
| M202L | 0.09 | 0.04 | 0.48 |
| F308G | 0.11 | 0.05 | 0.48 |
| S345G + F346V + P347* + G348* + S349A + G350A | 0.06 | 0.03 | 0.47 |
| R50E | 0.04 | 0.02 | 0.47 |
| W38F + A144R + Y180F + F228L + F229L | 0.07 | 0.03 | 0.44 |
| F253L | 0.06 | 0.02 | 0.44 |
| A144R + T188A + S345G + F346V + P347* + G348* + S349A + G350A | 0.06 | 0.03 | 0.43 |
| Y104F | 0.13 | 0.06 | 0.42 |
| Y18I | 0.07 | 0.03 | 0.42 |
| Y180F + F228L + F229L + Y287R | 0.06 | 0.03 | 0.41 |
| T188A | 0.10 | 0.04 | 0.40 |
| W38F | 0.08 | 0.03 | 0.40 |
| Y180F + F228L + F229L + S345G + F346V + G348* + P347* + S349A + G350A | 0.09 | 0.03 | 0.39 |
| M152L | 0.10 | 0.04 | 0.39 |
| W195F | 0.03 | 0.01 | 0.39 |
| Y258F | 0.08 | 0.03 | 0.38 |
| Y180F + F228L + F229L | 0.10 | 0.04 | 0.38 |
| H256S | 0.07 | 0.03 | 0.37 |
| Q167E | 0.06 | 0.02 | 0.36 |
| Y281F | 0.08 | 0.03 | 0.35 |
| F224G | 0.05 | 0.02 | 0.35 |
| W38F + Y180F + F228L + F229L + Y258F | 0.08 | 0.03 | 0.35 |
| T100K + H107F + L114I | 0.07 | 0.02 | 0.34 |
| Y104F + Y180F + F228L + F229L | 0.10 | 0.03 | 0.33 |
| Wildtype | 0.06 | 0.02 | 0.32 |

Example 4

Reduced Catalase Activity

Concept: Variants with reduced activity for dismutation of hydrogen peroxide relative to NBD activity are considered to have reduced activity.

The catalase side activity for dismutation of hydrogen peroxide into oxygen and water was monitored spectrophotometrically at 240 nm at the following conditions: 10 mM H2O2 was incubated with 0.005 mg EP/mL in a 50 mM phosphate buffer, pH 6.5 at room temperature. The reaction mixtures of 0.2 mL in volume were measured in a 96 well microtitre plate at room temperature on a SpectraMax S384plus microtitre plate reader (Molecular Devices LLC, Sunnyvale, Calif., USA). Extra 10 μL of 200 mM H2O2 was added two times. The concentration of H2O2 after each treatment with H2O2 was determined from the absorbance at 240 nm substracted the absorbance of enzyme samples without addition of H2O2 using the extinction coefficient for H2O2 of 0.0394 mM$^{-1}$ cm$^{-1}$ (Nelson and Kiesow 1972). The conversion of H2O2 after the three doses was calculated from the measured peroxide concentrations of the samples compared to blanks without enzyme.

The best variants were selected using the following procedure: Low activity variants that formed less than 0.03 mM 4-nitrocatechol at 0.5 mM H2O2 were first removed from the data set. The variants were then sorted according to the catalase activity relative to NBD activity at 0.5 mM H2O2 and compared against the wildtype.

strate or in peroxidase mode forming free radicals. Variants showing lower peroxidase activity relative to NBD activity are considered to have reduced peroxidase activity.

Peroxidase activity for oxidation of 2,2'-azinobis-(3-ethylbenzothiazoline-6-sulphonic acid) (ABTS) was monitored at 405 nm at the following conditions: 0.5 mM ABTS was reacted with 0.5 mM H2O2 in the presence of 0.002 mg

TABLE 2

Peroxygenase variants having reduced catalase activity.

| Peroxygenase variant (amino acid changes) | Catalase activity (% H2O2 consumed after third dosage) | NBD activity at 0.5 mM H2O2 | Ratio of catalase/NBD activity |
|---|---|---|---|
| A144R + F163C + Y180F + T188A + S345G + F346V + G348* + P347* + S349A + G350A | 14% | 0.04 | 3.85 |
| W38F + Y180F + F224L + F228L + F229L | 27% | 0.06 | 4.27 |
| Y180F + F224L + F229L | 22% | 0.05 | 4.30 |
| W38F + A144R + Y180F + F228L + F229L | 34% | 0.07 | 4.69 |
| A144R + Y180F + F228L + F229L | 48% | 0.10 | 4.95 |
| A144R + Y180F | 60% | 0.12 | 4.96 |
| M94F + Y180F + F228L + F229L | 55% | 0.10 | 5.44 |
| Y180F + F228L + F229L + L317N + T319S | 41% | 0.07 | 5.57 |
| W38F + Y180F + F228L + F229L | 71% | 0.12 | 6.04 |
| Y104F + Y180F + F228L + F229L | 60% | 0.10 | 6.18 |
| F146L + F228L + S345G + F346V + G348* + P347* + S349A + G350A | 10% | 0.02 | 6.34 |
| Y180F + F228L + F229L + S345G + F346V + G348* + P347* + S349A + G350A | 62% | 0.09 | 6.95 |
| T188A | 67% | 0.10 | 7.01 |
| W38F + Y180F + S222A + F228L + F229L | 95% | 0.13 | 7.16 |
| Y215F | 99% | 0.14 | 7.31 |
| Y180F + F224L + F228L + F229L | 43% | 0.06 | 7.33 |
| I98V | 48% | 0.06 | 7.36 |
| Y104F | 99% | 0.13 | 7.40 |
| A144R + T188A + S345G + F346V + P347* + G348* + S349A + G350A | 47% | 0.06 | 7.61 |
| A144R + Y180F + F224L + F228L | 40% | 0.05 | 7.62 |
| A144R + Y180F + S345G + F346V + G348* + P347* + S349A + G350A | 45% | 0.06 | 7.67 |
| F308G | 81% | 0.11 | 7.69 |
| F228L + S345G + F346V + P347* + G348* + S349A + G350A | 64% | 0.08 | 7.80 |
| F229L | 98% | 0.13 | 7.85 |
| W38F + Y180F + F224L + F228L + F229L + Y258F | 25% | 0.03 | 7.87 |
| Y72F | 99% | 0.13 | 7.93 |
| A144R | 59% | 0.07 | 8.04 |
| Q167E | 53% | 0.06 | 8.18 |
| Y180F + F228L + F229L | 79% | 0.10 | 8.31 |
| W38F + Y180F + F228L + F229L + Y258F | 69% | 0.08 | 8.60 |
| F228L | 68% | 0.08 | 9.03 |
| A144R + Y180F + T188A + F308L + S345G + F346V + G348* + P347* + S349A + G350A | 46% | 0.05 | 9.10 |
| M94F | 90% | 0.10 | 9.19 |
| F228L + F308L + S345G + F346V + G348* + P347* + S349A + G350A | 92% | 0.10 | 9.26 |
| M152L | 95% | 0.10 | 9.29 |
| Y258F | 76% | 0.08 | 9.60 |
| F163C + F228L + S345G + F346V + G348* + P347* + S349A + G350A | 99% | 0.10 | 9.71 |
| Y281F | 76% | 0.08 | 9.82 |
| Y180F + F228L + F229L + Y287R | 63% | 0.06 | 9.86 |
| W38F + Y180F + F224L + F228L + F229L | 40% | 0.04 | 9.96 |
| F224G | 48% | 0.05 | 9.97 |
| H256S | 75% | 0.07 | 10.09 |
| M246L | 99% | 0.10 | 10.13 |
| Y180F + F224L + F228L | 41% | 0.04 | 10.18 |
| W38F | 87% | 0.08 | 10.39 |
| E16D | 78% | 0.07 | 10.55 |
| Wildtype | 64% | 0.06 | 10.59 |

Example 5

Reduced Peroxidase Activity

Concept: Peroxygenases has the ability to act either in monooxygenase mode resulting in hydroxylation of a sub- EP/mL in 50 mM acetate buffer pH 5.0. The reaction mixtures of 0.2 mL in volume were measured in a 96 well microtitre plate at room temperature on a SpectraMax S384plus microtitre plate reader (Molecular Devices LLC, Sunnyvale, Calif., USA). The concentration of oxidized ABTS was determined from the absorbance at 405 nm after 1.5 minute of reaction using an extinction coefficient of 36.6 mM$^{-1}$ cm$^{-1}$.

The best variants were selected using the following procedure: Low activity variants that formed less than 0.03 mM 4-nitrocatechol at 0.5 mM H2O2 were first removed from the data set. The variants were then sorted according to the peroxidase activity relative to NBD activity at 0.5 mM H2O2 and compared against the wildtype.

TABLE 3

Peroxygenase variants having reduced peroxidase activity.

| Peroxygenase variant (amino acid changes) | NBD activity at 0.5 mM H2O2 | ABTS activity | Ratio of ABTS activity/NBD activity |
|---|---|---|---|
| W38F + Y180F + F224L + F228L + F229L | 0.06 | 0.03 | 0.49 |
| F228L | 0.08 | 0.05 | 0.66 |
| Y180F + F224L + F229L | 0.05 | 0.04 | 0.77 |
| W38F + Y180F + F224L + F228L + F229L + Y258F | 0.03 | 0.03 | 0.91 |
| M94F + Y180F + F228L + F229L | 0.10 | 0.11 | 1.04 |
| Y180F + F224L + F228L + F229L | 0.06 | 0.07 | 1.19 |
| W38F + A144R + Y180F + F228L + F229L | 0.07 | 0.11 | 1.46 |
| Y180F + F228L + F229L + L317N + T319S | 0.07 | 0.11 | 1.50 |
| A144R + Y180F + F224L + F228L | 0.05 | 0.09 | 1.69 |
| Y180F + F224L + F228L | 0.04 | 0.07 | 1.76 |
| C103S + H102R + W38F + A144R + Y180F | 0.03 | 0.07 | 2.12 |
| W38F + Y180F + F228L + F229L | 0.12 | 0.25 | 2.16 |
| I98L | 0.05 | 0.10 | 2.21 |
| A144R + Y180F + F228L + F229L | 0.10 | 0.27 | 2.75 |
| W38F + Y180F + F228L + F229L + Y258F | 0.08 | 0.23 | 2.82 |
| Y104F + Y180F + F228L + F229L | 0.10 | 0.28 | 2.86 |
| Y180F + F228L + F229L | 0.10 | 0.37 | 3.88 |
| Y180F + F228L + F229L + Y287R | 0.06 | 0.25 | 3.91 |
| F224G | 0.05 | 0.20 | 4.07 |
| Y18I | 0.07 | 0.31 | 4.30 |
| T100K + H107F + L114I | 0.07 | 0.28 | 4.32 |
| W195F | 0.03 | 0.15 | 4.49 |
| T188A | 0.10 | 0.46 | 4.76 |
| M94F | 0.10 | 0.47 | 4.80 |
| Q167E | 0.06 | 0.34 | 5.18 |
| A144R + Y180F | 0.12 | 0.68 | 5.65 |
| F253L | 0.06 | 0.35 | 6.20 |
| A144R | 0.07 | 0.46 | 6.24 |
| E16D | 0.07 | 0.48 | 6.47 |
| Y180F + F228L + F229L + S345G + F346V + G348* + P347* + S349A + G350A | 0.09 | 0.61 | 6.85 |
| R50E | 0.04 | 0.26 | 7.17 |
| H256S | 0.07 | 0.54 | 7.23 |
| F228L + S345G + F346V + P347* + G348* + S349A + G350A | 0.08 | 0.61 | 7.43 |
| F229L | 0.13 | 0.96 | 7.63 |
| Y281F | 0.08 | 0.59 | 7.64 |
| Wildtype | 0.06 | 0.46 | 7.69 |

Example 6

Improved Activity on Veratryl Alcohol

Concept: Variants with increased activity on veratryl alcohol are considered to have altered the relative substrate specificity.

The oxidation of veratryl alcohol (3,4-dimethoxybenzyl alcohol) to veratryl aldehyde (3,4-dimethoxybenzyl aldehyde) was monitored spectrophotometrically at 310 nm at the following conditions: 1 mM veratryl alcohol was reacted with 0.5 mM H2O2 in the presence of 0.01 mg EP/mL in 50 mM phosphate buffer pH 6.5. The reaction mixtures of 0.2 mL in volume were measured in a 96 well microtitre plate at room temperature on a SpectraMax S384plus microtitre plate reader (Molecular Devices LLC, Sunnyvale, Calif., USA). The concentration of veratryl aldehyde was determined from the absorbance at 310 nm after 5 minutes of reaction and quantified by calibration with authentic standards.

The best variants were selected using the following procedure: Low activity variants that formed less than 0.03 mM 4-nitrocatechol at 0.5 mM H2O2 were first removed from the data set. The variants were then sorted according to the activity on veratryl alcohol relative to NBD at 0.5 mM H2O2.

TABLE 4

Peroxygenase variants having improved activity on veratryl alcohol.

| Peroxygenase variant (amino acid changes) | NBD activity at 0.5 mM H2O2 | Veratryl alcohol activity | Ratio of veratryl alcohol/NBD activity |
|---|---|---|---|
| Y180F + F224L + F228L | 0.04 | 0.27 | 6.66 |
| W38F + Y180F + F224L + F228L + F229L + Y258F | 0.03 | 0.17 | 5.37 |
| Y180F + F224L + F229L | 0.05 | 0.26 | 4.98 |
| A144R + Y180F + F224L + F228L | 0.05 | 0.25 | 4.79 |
| Y180F + F224L + F228L + F229L | 0.06 | 0.27 | 4.65 |
| W195F | 0.03 | 0.11 | 3.44 |
| C103S + H102R + W38F + A144R + Y180F | 0.03 | 0.10 | 3.09 |

TABLE 4-continued

Peroxygenase variants having improved activity on veratryl alcohol.

| Peroxygenase variant (amino acid changes) | NBD activity at 0.5 mM H2O2 | Veratryl alcohol activity | Ratio of veratryl alcohol/ NBD activity |
|---|---|---|---|
| W38F + Y180F + F224L + F228L + F229L | 0.06 | 0.18 | 2.92 |
| F92L | 0.04 | 0.11 | 2.50 |
| R50E | 0.04 | 0.09 | 2.48 |
| F224G | 0.05 | 0.12 | 2.38 |
| F253L | 0.06 | 0.13 | 2.24 |
| I98V | 0.06 | 0.13 | 2.07 |
| A144R + Y180F + S345G + F346V + G348* + P347* + S349A + G350A | 0.06 | 0.10 | 1.79 |
| S345G + F346V + P347* + G348* + S349A + G350A | 0.06 | 0.09 | 1.65 |
| Wildtype | 0.06 | 0.10 | 1.64 |

Example 7

Improved Activity on Cyclohexane

Concept: Peroxygenases are able to oxidize cyclohexane to a mixture of cyclohexanol and cyclohexanone using hydrogen peroxide. Variants producing higher yields in oxidation of cyclohexane compared to the wildtype enzyme are considered to have improved performance on cyclohexane oxidation.

The oxidation of cyclohexane by peroxygenase was assayed as follows: Reagents were mixed in closed glass vials by magnetic stirring at room temperature for three hours, to reach a total volume of 800 µL and final concentrations of: 50 g/L cyclohexane, 100 mM pH 6.0 phosphate buffer, 20% v/v acetonitrile, 0.1 mg EP/mL and 250 mM H2O2. The hydrogen peroxide was dosed in continuously using a syringe pump over the three hours of reaction. At the end of the reaction the samples were extracted with 800 µL of ethyl acetate containing 2 mM n-decane as internal standard and concentrations of cyclohexanol and cyclohexanone were determined by Gas Chromatography Mass Detection as follows: Samples were injected in split mode (50:1) on a Zebron ZB-1 ms column (30 m, 250 µm, 0.25 µm) from Phenomenex (Torrance Calif., USA). Compounds were eluted with 1.0 mL/min Helium using the following temperature program: 45° C. (for 2 min), 45-80° C. at 10° C./min, 80-260° C. at 40° C./min (hold for 1 min). Peaks were identified by comparing the mass spectra with spectra from the library available in the GC software. Product concentrations were quantified by external calibration with authentic standards using n-decane as internal standard. The total product concentration was determined as the sum of cyclohexane and cyclohexanone concentration.

TABLE 5

Peroxygenase variants having improved performance on cyclohexane oxidation.

| Peroxygenase variant (amino acid changes) | Total product concentration (mM) |
|---|---|
| Y104F | 71 |
| W38F Y180F S222A F228L F229L | 70 |
| E16D | 61 |
| H256S | 50 |
| Wildtype | 44 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A peroxygenase variant, comprising a substitution at one or more positions corresponding to positions E16, Y18, W38, R50, Y72, F92, M94, I98, T100, H102, C103, Y104, H107, L114, A144, M152, Q167, T188, W195, Y215, F224, F228, F229, M246, F253, H256, Y258, Y281, Y287, F308, L317, S345, F346, P347, G348, S349, and G350 of SEQ ID NO: 2, wherein the variant has peroxygenase activity and has at least 90% but less than 100% sequence identity to amino acids 19-362 of SEQ ID NO: 2.

2. The variant of claim 1, which has at least 95% sequence identity to amino acids 19-362 of SEQ ID NO: 2.

3. The variant of claim 1, which has at least 97% sequence identity to amino acids 19-362 of SEQ ID NO: 2.

4. The variant of claim 1, which has at least 99% sequence identity to amino acids 19-362 of SEQ ID NO: 2.

5. A polynucleotide encoding the variant of claim 1.

6. A nucleic acid construct or expression vector comprising the polynucleotide of claim 5.

7. A host cell comprising the polynucleotide of claim 5.

8. A method of producing a peroxygenase variant, comprising:
   (a) cultivating the host cell of claim 7 under conditions suitable for expression of the variant; and
   (b) recovering the variant.

9. A method for hydroxylation in position 2 or 3 of the terminal end of an acyl group of a lipid, comprising contacting the lipid with hydrogen peroxide and a peroxygenase variant of claim 1.

10. A method for introducing a hydroxy or a keto group at the second or third carbon of at least two ends of a substituted or unsubstituted, linear or branched, aliphatic hydrocarbon having at least five carbons and having at least one hydrogen attached to said second or third carbon, comprising contacting the aliphatic hydrocarbon with hydrogen peroxide and a peroxygenase variant of claim 1.

11. A method for hydroxylation in position 2 or 3 of either end of a substituted or unsubstituted, linear or branched, aliphatic hydrocarbon having at least 3 carbons and having a hydrogen attached to the carbon in position 2 or 3, comprising contacting the aliphatic hydrocarbon with hydrogen peroxide and a peroxygenase variant of claim 1.

12. The method of claim 11, wherein the aliphatic hydrocarbon is an alkane.

13. The method of claim 12, wherein the alkane is pentane, hexane, heptane, octane, nonane, decane, undecane, dodecane, tridecane, tetradecane, pentadecane or hexadecane, or isomers thereof.

14. The method of claim 11, wherein the aliphatic hydrocarbon is unsubstituted.

15. The method of claim 11, wherein the aliphatic hydrocarbon is linear.

16. The method of claim 11, wherein the aliphatic hydrocarbon is a fatty acid.

17. A peroxygenase variant, comprising a substitution at one or more positions corresponding to positions P28, P31, F146, F163, F216, and S222 of SEQ ID NO: 2, wherein the variant has peroxygenase activity and has at least 90% but less than 100% sequence identity to amino acids 19-362 of SEQ ID NO: 2.

18. The variant of claim 17, which has at least 95% sequence identity to amino acids 19-362 of SEQ ID NO: 2.

19. The variant of claim 17, which has at least 97% sequence identity to amino acids 19-362 of SEQ ID NO: 2.

20. The variant of claim 17, which has at least 99% sequence identity to amino acids 19-362 of SEQ ID NO: 2.

21. The variant of claim 17, which has an improved property relative to a corresponding unsubstituted peroxygenase, wherein the improved property is selected from the group consisting of improved oxidation stability, improved storage stability, reduced catalase activity, reduced peroxidase activity, improved activity on veratryl alcohol, and improved activity on cyclohexane.

* * * * *